US010774296B2

(12) United States Patent
Carter et al.

(10) Patent No.: US 10,774,296 B2
(45) Date of Patent: Sep. 15, 2020

(54) LIDDED CELL CULTURE DEVICES WITH IMPROVED HANDLING PERFORMANCE AND METHODS FOR USING SAME

(71) Applicant: Corning Incorporated, Corning, NY (US)

(72) Inventors: Thomas Landon Carter, Cary, NC (US); Gregory Scott Jordan, Wake Forest, NC (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 15/476,109

(22) Filed: Mar. 31, 2017

(65) Prior Publication Data

US 2017/0283757 A1    Oct. 5, 2017

Related U.S. Application Data

(60) Provisional application No. 62/318,425, filed on Apr. 5, 2016.

(51) Int. Cl.
| | | |
|---|---|---|
| *C12M 1/22* | (2006.01) | |
| *C12M 1/00* | (2006.01) | |
| *C12M 3/00* | (2006.01) | |
| *C12M 1/32* | (2006.01) | |

(52) U.S. Cl.
CPC ............ *C12M 23/10* (2013.01); *C12M 23/12* (2013.01); *C12M 23/38* (2013.01); *C12M 23/54* (2013.01)

(58) Field of Classification Search
CPC ....... C12M 23/10; C12M 23/12; C12M 23/38
See application file for complete search history.

(56) References Cited

U.S. PATENT DOCUMENTS

| | | | | |
|---|---|---|---|---|
| 3,198,713 | A | * | 8/1965 | McCormick ........... C12M 23/10 206/509 |
| 3,203,870 | A | | 8/1965 | Andelin |
| 3,597,326 | A | * | 8/1971 | Liner ..................... C12M 23/10 435/305.3 |
| 4,038,149 | A | * | 7/1977 | Liner ................. G01N 33/5304 435/305.3 |
| 4,204,045 | A | * | 5/1980 | Kjellander ............. C12M 23/04 220/555 |
| 4,598,050 | A | | 7/1986 | Brown |
| 5,725,123 | A | * | 3/1998 | Otto-Nagels ........ B65D 50/045 215/230 |
| 5,817,510 | A | * | 10/1998 | Pandey ................. B01L 3/5025 435/305.3 |

(Continued)

FOREIGN PATENT DOCUMENTS

| | | | |
|---|---|---|---|
| JP | 2004337057 A | 12/2004 | |
| JP | 2010000080 A  * | 1/2010 | ............ C12M 23/10 |

OTHER PUBLICATIONS

English language machine translation of JP2010000080, pp. 1-13. (Access Jun. 25, 2018). (Year: 2018).*

*Primary Examiner* — William H. Beisner
(74) *Attorney, Agent, or Firm* — Annie J. Kock

(57) ABSTRACT

Cell culture devices are described herein that have notched lids, notched lids with corresponding gripping pads included on their bases, or gripping tabs included on their bases to minimize or eliminate the need for a user to contact a lid when attempting to lift or move a lidded cell culture device. In addition, methods for using the cell culture devices are also described herein.

10 Claims, 9 Drawing Sheets

(56) References Cited

U.S. PATENT DOCUMENTS

| 9,040,293 B2 | 5/2015 | Gulzow et al. |
| 2010/0093075 A1 | 4/2010 | Muller |
| 2011/0174820 A1 | 7/2011 | Giles |

\* cited by examiner

LIDDED CELL CULTURE DEVICES WITH IMPROVED HANDLING PERFORMANCE AND METHODS FOR USING SAME

This application claims the benefit of priority under 35 U.S.C. § 119 of U.S. Provisional Application Ser. No. 62/318,425 filed on Apr. 5, 2016, the content of which is relied upon and incorporated herein by reference in its entirety.

TECHNICAL FIELD

The present disclosure generally relates to cell culture devices (e.g. multiple well plates, microwell plates, petri dishes, in vitro fertilization dishes, and in vitro fertilization plates) and methods for using the cell culture devices. The cell culture devices have notched lids, notched lids with corresponding gripping pads included on their bases, or gripping tabs included on their bases to minimize or eliminate the need for a user to contact the lid when attempting to lift or move a lidded cell culture device.

BACKGROUND

Current cell culture devices (e.g. cell culture plates, cell culture dishes) are designed as lid and base systems wherein a separate base and lid are paired together to provide a cell culture environment. The base provides the cell culturing area of the device while the lid acts as a cover to protect the cell culturing area from particulate and microbiological contamination and, in some applications, to limit evaporation of media from the cell culturing area. Current cell culture devices include lid designs with a full skirt that generally inhibit the user from gaining easy capture of the base between a thumb and finger to allow the device to be easily picked up. The low profile (i.e. low side wall height) of the base of these devices when combined with the relatively long skirt of the lid often result in a situation where the lid is presented as the major contact surface for the user as they attempt to pick the device up from a storage location, a work surface, or a stack of like devices. In the best case outcome, the user exercises extreme care to capture the lid and base as a pair in order to move the pair from one place to another. In a less ideal outcome, the user inadvertently removes the lid during the device manipulation which, in turn, can result in cell culture contamination. In the worst case outcome, the full skirt of the lid inhibits the user from making robust contact with the base and leads to the user dropping the device during manipulation. Hence, there is a need for an improved design of lidded cell culture devices and this need is more readily apparent in view of the following detailed discussion about current cell culture devices and some of the additional problems associated with current cell culture devices.

Typically, cell culture plates have square or rectangular footprints. Examples of cell culture plates are multiple well assay plates, microwell plates, and in vitro fertilization (IVF) plates. In contrast, cell culture dishes typically have circular footprints. An example of a cell culture dish is the common petri dish which has been used in the laboratory environment since the 1880s. FIG. 1 (PRIOR ART) provides a representation of an exemplary traditional petri dish 100. The traditional petri dish 100 has a circular base 102 and a circular lid 104. The circular base 102 has a flat bottom panel 106 and a base sidewall 108 extending substantially perpendicularly upward from the flat bottom panel 106. The circular lid 104 has a lid panel 110 and a lid sidewall 112 extending substantially perpendicularly downward from the lid panel 110. The inner diameter of the of the lid sidewall 112 is greater than the outer diameter of the base sidewall 108 such that the circular lid 104 when set on the circular base 102 covers the circular base 102 with the lid sidewall 112 extending over and covering the top of the base sidewall 108. The base sidewall 108 is of greater height than the depth of the lid sidewall 112.

Lidded cell culture devices (e.g. cell culture plates, cell culture dishes) are used in various fields including, for example, microbiology, cell culturing, tissue culturing, cell assays, and IVF. The currently marketed designs for cell culture dishes include fully skirted lids that have larger diameters than their respective bases. The currently marketed designs for cell culture plates include fully skirted lids with overall widths and lengths greater than their respective bases. The fully skirted design approach provides a lid that wraps over the side wall of the base to keep the lid located over the base. However, this lid design when combined with the standard low profile base design typically results in the lid skirt obscuring the base sidewall making it difficult to lift the plate or dish concurrent with its mounted and paired lid. Oftentimes the lid must be removed from the plate or dish in order lift and move the plate or dish base. Alternately, the user must carefully pinch both the lid and base between their thumb and finger concurrently to lift both the lid and base as a pair. As the overall dimension of the lid is greater than the overall dimension of the base and as the profile of the base is typically low, trying to concurrently capture both the lid and base by pinching a thumb and finger against them is very difficult. Often the user will rock the cell culture device off of the work surface slightly to gain contact of their thumb or finger to a small portion of the height of the base that is not obscured by the lid. This is especially true for cell culture dishes, as currently marketed dish designs include lid skirts of greater diameter than their paired base skirt diameter. Media spillage can readily occur as the user rocks the cell culture device in their attempt to capture both the lid and base. Hence, improved designs of cell culture devices are needed to address this problem.

Most current cell culture plate designs include a base skirt of sufficient height to allow the user to pick up the base and lid concurrently by capturing the base skirt between their thumb and finger. These plate designs, however, require the total height of the base to be greater than is absolutely required, include a lower profile lid skirt, or provide a lid skirt that is shorter than the ideal height to allow easy gripping by a thumb and finger. Even with this base skirt design, plate users often experience difficulty moving the cell culture plate without risk of inadvertently removing its paired lid. Or, avoiding this issue, the user has to make a concerted effort to capture the base skirt between their thumb and finger due to the relatively low profile of the base skirt. Current designs for cell culture dishes do not include a base skirt, but rather depend on the manual agility of the user to pinch a portion of both the lid skirt and base wall concurrently in order to lift a paired base and lid. The difficulty of capturing the lid and base concurrently in all of these cell culture dish and plate designs is compounded by the fact that the user is typically wearing plastic gloves and manipulating the cell culture device within the tight confines of a laboratory laminar flow hood. Hence, improved designs of cell culture devices are needed to address this problem.

Further, it is well understood that effective cell culturing entails the minimization of the potential introduction of contaminants such as particulate or unintended microbes to the cell culturing area within the cell culture devices. As the probability of contaminating the cell culturing area within a cell culture device is directly proportional to the number of times that the device lid is removed during the cell culturing process, it is evident that cell culture device designs should minimize the frequency that lids are unnecessarily removed from their bases. However, current cell culture devices are designed with lids that protrude beyond the base walls of the devices and this common lid and base design makes it difficult for the user to lift the lidded pair concurrently. As a result, current cell culture devices often experience unnecessary lid removal and, therefore, unnecessary exposure to contaminants when simply trying to transfer the device from one place to another within the laboratory environment. Hence, improved designs of cell culture devices are needed to address this problem.

Additionally, the user often performs other operations (e.g. pipetting, visual inspection of cells, microscopic inspection of cells) during cell culturing operations. During pipetting, the user typically holds a pipettor in their dominant hand while manipulating stacks and individual cell culture devices with their other, i.e. non-dominant, hand. This leaves the user in the undesirable position of handling a cell culture device that is often small and difficult to lift as a lid and base pair using their non-dominant hand. Hence, improved designs of cell culture devices are needed to address this problem.

Finally, though not necessarily a best practice during cell culturing processes, there are occasions when the user may place the lid of the cell culture device on a laboratory work surface. Current lid designs include a full skirt that leads to the potential that the lid becomes stuck to the laboratory work surface due to the creation of an area of lower air pressure (i.e. a relative vacuum) beneath the lid. This is especially true when the lid is removed from the base and set down such that the lid skirt is placed in contact with a wetted work surface. Hence, improved designs of cell culture devices are needed to address this problem.

Designers and manufacturers of cell culture devices have tried to address at least some of these problems by, for example, designing higher profile (i.e. higher side wall height) bases and/or shorter skirts on lids so as to minimize the lid skirt profile in comparison to the base sidewall profile. However, improved designs are still needed to address the aforementioned problems associated with the current lidded cell culture devices (e.g. cell culture plates, cell culture dishes).

SUMMARY

Cell culture devices and methods for using the cell culture devices which address the aforementioned problems are described in the independent claims of the present application. Advantageous embodiments of the cell culture devices and the methods for using the cell culture devices are described in the dependent claims.

In one aspect, the present disclosure provides a cell culture device which comprises a base having a base sidewall. The cell culture device further comprises a lid configured to fit over the base. The lid has a top panel and a lid sidewall (i.e. skirt) extending downwardly from the top panel, where the lid sidewall is connected to the top panel and has a bottom edge. The lid sidewall also has at least two notches located therein, wherein each one of the notches is sized to fit a human finger. That is, the notches are structured to allow a user to grip the plate exposed by the notches. Further, the present disclosure provides a method for using this cell culture device. The method comprises steps of gripping the base through at least two of the notches in the lid when the lid is fitted over the base, and moving the gripped base and the fitted lid from a first location to a second location. Further, the method may comprise a step of removing the lid by gripping the lid at a location other than at the at least two notches.

In another aspect, the present disclosure provides a cell culture device which comprises a base having a base sidewall. The cell culture device further comprises a lid configured to fit over the base. The lid has a top panel and a lid sidewall (i.e. skirt) extending downwardly from the top panel, where the lid sidewall is connected to the top panel and has a bottom edge. The lid sidewall also has at least two notches located therein, wherein each one of the notches is sized to fit a human finger. That is, the notches are structured to allow a user to grip the plate exposed by the notches. In addition, the cell culture device's base sidewall has at least two gripping pads (e.g. finger pads), where each one of the gripping pads has at least a portion thereof present within a corresponding one of the notches when the lid is fitted over the base. Further, the present disclosure provides a method for using this cell culture device. The method comprises steps of gripping at least two gripping pads through at least two of the notches in the lid when the lid is fitted over the base, and moving the gripped base and the fitted lid from a first location to a second location. Further, the method may comprise a step of removing the lid by gripping the lid at a location other than at the at least two notches.

In yet another aspect, the present disclosure provides a cell culture device which comprises a base having a base sidewall. The cell culture device further comprises a lid configured to fit over the base. The lid has a top panel and a lid sidewall (i.e. skirt) extending downwardly from the top panel, where the lid sidewall is connected to the top panel and has a bottom edge. The cell culture device's base sidewall further has an outer wall, where the outer wall has at least two gripping tabs (e.g. finger tabs) extending therefrom, where each of the gripping tabs have an inner side where a gap is present between the outer side of the base sidewall and the inner side of each of the gripping tabs, and where each of the gaps is sized to receive the lid sidewall when the lid is fitted over the base. Further, the present disclosure provides a method for using this cell culture device. The method comprises steps of gripping at least two of the gripping tabs when the lid is fitted over the base, and moving the gripped base and the fitted lid from a first location to a second location. Further, the method may comprise a step of removing the lid by gripping the lid at a location other than at the at least two gripping tabs.

Additional aspects of the disclosure will be set forth, in part, in the detailed description, figures and any claims which follow, and in part will be derived from the detailed description, or can be learned by practice of the disclosure. It is to be understood that both the foregoing general description and the following detailed description are exemplary and explanatory only and are not restrictive of the disclosure as disclosed.

BRIEF DESCRIPTION OF THE DRAWINGS

A more complete understanding of the present disclosure may be had by reference to the following detailed description when taken in conjunction with the accompanying drawings wherein.

DETAILED DESCRIPTION

Certain illustrative embodiments and configurations of cell culture devices are provided and described in detail below. It should be understood that the present disclosure is not limited to these particular embodiments of the cell culture devices. It should also be understood that the cell culture devices may be used in a wide variety of scientific applications where dishes and plates find use such as, for example, crystal growth, plant germination, microbiology studies, study of small animals, drying fluids, carrying or storing samples, microscopic studies, and the like.

What is required in the field, and what the present disclosure provides, are cell culture devices (e.g. cell culture plates and cell culture dishes) that have been designed to enable the user to lift the base and lid as a pair through primary contact with the base while still providing the user the ability to lift and remove the lid by itself from the base to allow the required laboratory activities to culture the cells within the device. The designs of the cell culture devices described herein address these needs and other needs through, for example, the embodiments that are generally discussed next and then described with respect to specific exemplary embodiments in more detail below with reference to FIGS. 2-8.

Figure 1:
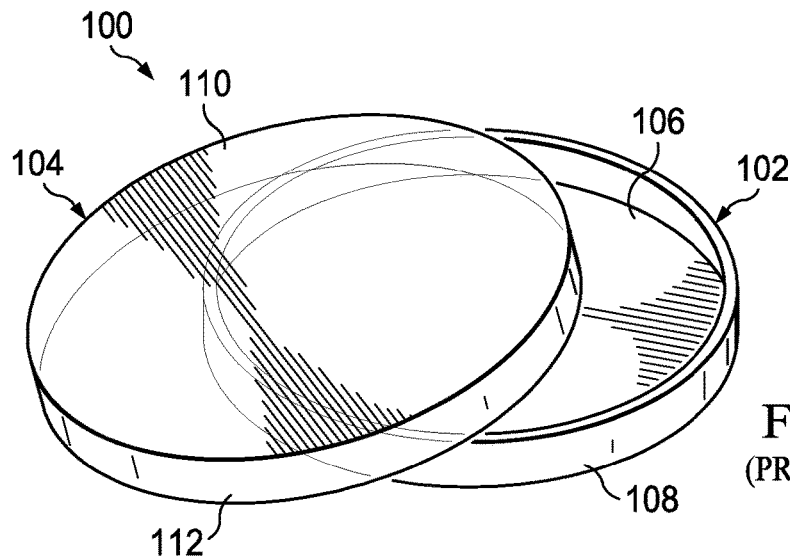
FIG. 1 (PRIOR ART) shows a diagram of an exemplary traditional petri dish.
Figure 2A:
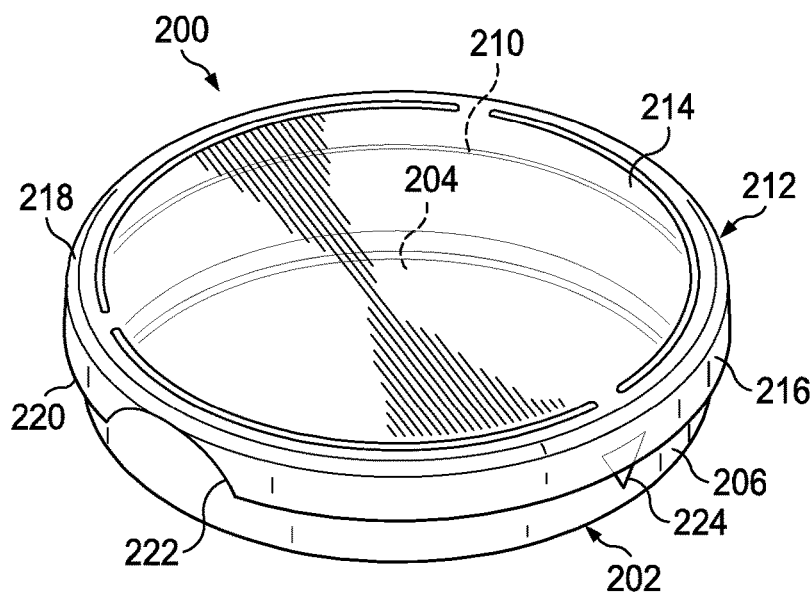
FIG. 2A shows an exemplary cell culture device having a lid with two notches that is fitted to a base in accordance with an embodiment of the present disclosure.

In the first approach, the cell culture device 200 comprises a base 202 having a bottom panel 204 and a base sidewall 206 extending upwardly from the bottom panel 204, where the base sidewall 206 is connected to the bottom panel 204 and has a top edge 210. The cell culture device 200 further comprises a lid 212 configured to fit over the base 202. The lid 212 having a top panel 214 and a lid sidewall 216 (i.e. skirt 216) extending downwardly from the top panel 214, where the lid sidewall 216 is connected to the top panel 214 at edge 218 and has a bottom edge 220. The lid sidewall 216 also has at least two notches 222 located therein, wherein each one of the notches 222 is sized to fit a human finger. That is, the notches are structured to allow a user to grip the plate exposed by the notches. FIGS. 2A-2B provide an example of this approach where the cell culture device 200 has a petri dish configuration. Note: the cell culture device 200 described herein has a specific configuration (i.e. dish configuration) and a base with a specific configuration (i.e. base sidewall connected to a bottom panel) but it should be appreciated that the new cell culture devices in accordance with the present disclosure are not required to have this specific configuration but instead can have different configurations (e.g. plate configuration) and different base configurations (e.g. base sidewall in form of a skirt) so long as the new cell culture device has, per this approach, a lid with at least two notches located therein, wherein each one of the notches is sized to fit a human finger.

In the second approach, the cell culture device 300, 400, 500, 600 and 700 comprises a base 302, 402, 502, 602, 702 having a base sidewall 306, 406, 506, 606, 706. The cell culture device 300, 400, 500, 600 and 700 further comprises a lid 312, 412, 512, 612, 712 configured to fit over the base 302, 402, 502, 602, 702. The lid 312, 412, 512, 612, 712 has a top panel 314, 414, 514, 614, 714 and a lid sidewall 316, 416, 516, 616, 716 (e.g. skirt 316, 416, 516, 616, 716) extending downwardly from the top panel 314, 414, 514, 614, 714, where the lid sidewall 316, 416, 516, 616, 716 is connected to the top panel 314, 414, 514, 614, 714 at edge 318, 418, 518, 618, 718 and has a bottom edge 320, 420, 520, 620, 720. The lid sidewall 316, 416, 516, 616, 716 also has at least two notches 322, 422, 522, 622, 722 located therein, wherein each one of the notches 322, 422, 522, 622, 722 is sized to fit a human finger. That is, the notches are structured to allow a user to grip the plate exposed by the notches. In addition, the cell culture device's base sidewall 306, 406, 506, 606, 706 has at least two gripping pads 324, 424, 524, 624, 724 extending therefrom or formed therein, where each one of the gripping pads 324, 424, 524, 624, 724 has at least a portion thereof present within a corresponding one of the notches 322, 422, 522, 622, 722 when the lid 312, 412, 512, 612, 712 is fitted over the base 302, 402, 502, 602, 702. FIGS. 3A-3B, 4A-4B, 5, 6, 7 provide examples of this approach where the cell culture device 300, 400, 500, 600, 700 respectively has a 4 well IVF plate configuration, a petri dish configuration, and three different multiwell plate configurations. Note: the cell culture devices 300, 400, 500, 600, 700 can have different configurations of bases 302, 402, 502, 602, 702 as described herein but they all have, per this particular approach, a base sidewall 306, 406, 506, 606, 706 with at least two gripping pads 324, 424, 524, 624, 724 extending therefrom or formed therein. In other words, the new cell culture devices in accordance with the present disclosure can have different configurations (e.g. dish configuration, plate configuration) and have different base configurations (e.g. base sidewalls attached to a base panel or in the form of a skirt) so long as the new cell culture device has, per this approach, a lid with at least two notches located therein, wherein each one of the notches is sized to fit a human finger and a base sidewall which has at least two gripping pads extending therefrom or formed therein.

Figure 8A:
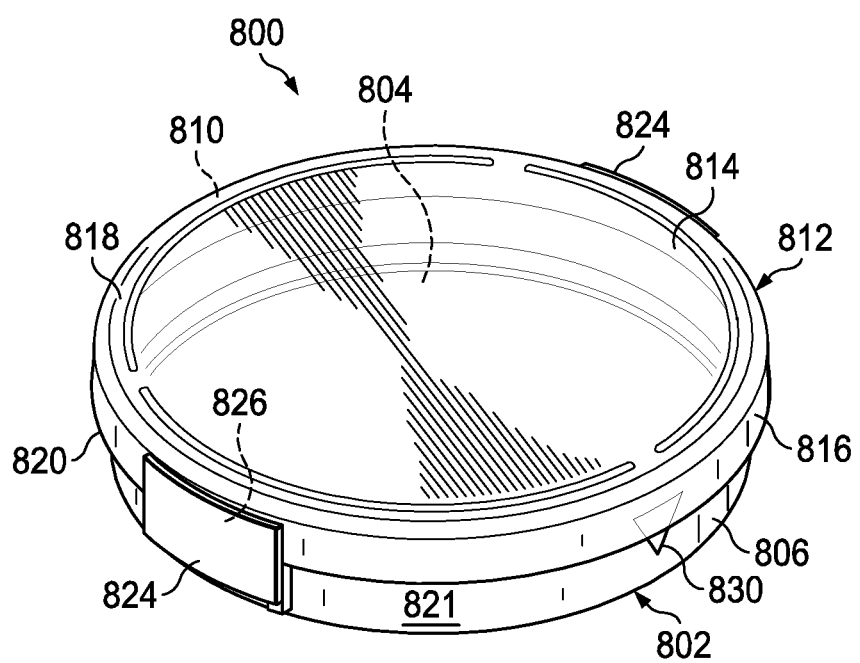
FIG. 8A shows an exemplary cell culture device having a dish base with two gripping tabs that is fitted to a lid without notches in accordance with an embodiment of the present disclosure.
Figure 8B:
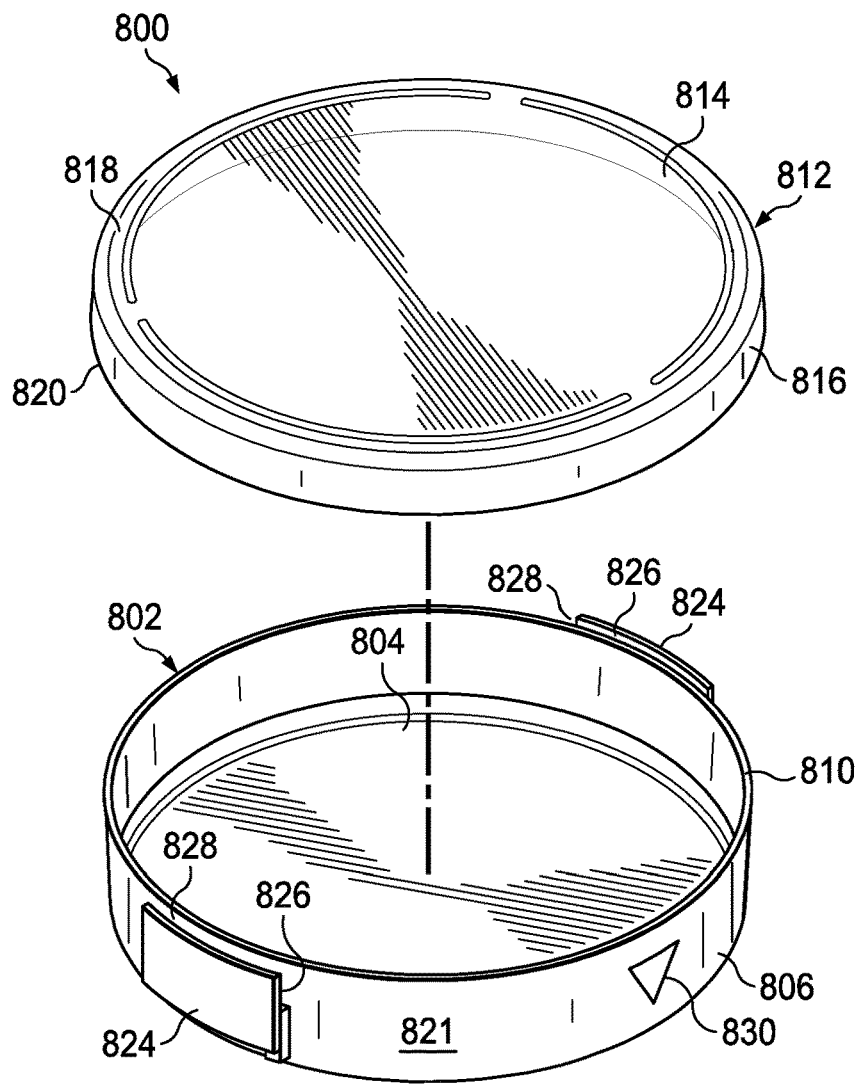
FIG. 8B shows the exemplary cell culture device of FIG. 8A with the lid removed from the base in accordance with an embodiment of the present disclosure.

In the third approach, the cell culture device 800 comprises a base 802 having a bottom panel 804 and a base sidewall 806 extending upwardly from the bottom panel 804, where the base sidewall 806 is connected to the bottom panel 804 and has a top edge 810. The cell culture device 800 further comprises a lid 812 configured to fit over the base 802. The lid 812 has a top panel 814 and a lid sidewall 816 (i.e. skirt 816) extending downwardly from the top panel 814, where the lid sidewall 816 is connected to the top panel 814 at edge 818 and has a bottom edge 820. The cell culture device's base sidewall 806 further has an outer surface 821 with at least two gripping tabs 824 extending therefrom, where each of the gripping tabs 824 have an inner side 826 where a gap 828 is present between the outer surface 821 of the base sidewall 806 and the inner side 826 of each of the gripping tabs 824, and where each of the gaps 828 is sized to receive the lid sidewall 816 when the lid 812 is fitted over the base 802. FIGS. 8A-8B provide an example of this approach where the cell culture device 800 has a petri dish configuration. Note: the cell culture device 800 described herein has a specific configuration (i.e. dish configuration) and a base with a specific configuration (i.e. base sidewall connected to a bottom panel) but it should be appreciated that the new cell culture devices in accordance with the present disclosure are not required to have this specific configuration but instead can have different configurations (e.g. plate configuration) and different base configurations (e.g. base sidewall in form of a skirt) so long as the new cell culture device per this approach has a base sidewall with at least two gripping tabs extending therefrom.

Each of these three approaches, provide specific gripping regions on the cell culture device 200, 300, 400, 500, 600, 700, 800 designed for the user to pinch between their thumb and finger (collectively "fingers") so as to lift the lidded device during required manipulation while still providing the user the ability to access areas of the lid's skirt for manipulation of the device's lid only. While the user will often use a thumb and finger, it should be understood that the gripping regions (e.g. base sidewall, gripping pads, gripping tabs) on the base can be gripped by any mechanism (e.g. two thumbs, two non-thumb fingers, another body part, a gripping device such as a clamp, tongs, robotic hand, robotic end of arm tooling, etc.).

Exemplary embodiments of the cell culture devices 200, 300, 400, 500 600, 700 and 800 are shown in FIGS. 2-8. It should be understood that the cell culture devices 200, 300, 400, 500 600, 700 and 800 and the methods for using the cell culture devices 200, 300, 400, 500 600, 700 and 800 described and shown herein are illustrative examples and that the present disclosure is not limited to these specific embodiments or their dimensions, volumes, configurations, or the like.

Referring to FIGS. 2A-2B, there is illustrated an exemplary cell culture device 200 configured in accordance with an embodiment of the present disclosure. The cell culture device 200 (which in this example has a petri dish configuration) comprises a base 202 having a bottom panel 204 and a base sidewall 206 extending upwardly from the bottom panel 204, where the base sidewall 206 is connected to the bottom panel 204 and has a top edge 210. The cell culture device 200 further comprises a lid 212 configured to fit over the base 202. The lid 212 has a top panel 214 and a lid sidewall 216 (i.e. skirt 216) extending downwardly from the top panel 214, where the lid sidewall 216 is connected to the top panel 214 and has a bottom edge 220. The lid sidewall 216 also has two notches 222 (more possible) located therein, wherein each one of the notches 222 is sized to fit a human finger.

The exemplary cell culture device 200 shown has a lid 212 with two notches 222 but it should be appreciated that the lid 212 can include more notches 222 (e.g. four notches 222) as desired. The notches 222 on the lid 212 provide unobscured access for a finger and thumb to contact the base sidewall 206 when the lid 212 and the base 202 are paired. When the two notches 222 are provided as shown on opposing sides of the lid 212, the notches 222 provide areas along the base sidewall 206 for the user to pinch between their thumb and finger to enable manipulation of the paired base 202 and lid 212. Further, the lid's notches 222 in this example are located on or very near the mass centerline of the cell culture device 200 to induce the user to lift the cell culture device 200 in a manner less likely to tip the device 200 during manipulation. Current cell culture devices do not include a lid with notches as shown herein and rely on the user to pinch the skirt of the base and lid concurrently in order manipulate the paired base and lid system. As will be understood by those skilled in the art, the use of the cell culture device 200 when the notched lid 212 is paired with the base 202 provides a base 202 and lid 212 system that is easier to lift when compared to currently available cell culture devices. Further, as will be understood by those skilled in the art, the use of the cell culture device 200 enables the user to pick up the paired base 202 and lid 212 by contacting the base sidewall 206 through the lid's notches 222 on opposing sides of the base 202, set the cell culture device 200 down on a work surface, then shift their finger and thumb to opposing points on the lid skirt 216 so as to deftly remove the lid 212 from the base 202 to enable pipetting or other laboratory work flow activities. Basically, the lid's notches 222 expose contact points along the base sidewall 206 to enable lifting of the paired lid 212 and base 202 while the lid skirt 216 provides contact areas for manipulation of the lid 212 separate from the base 202. Further, FIG. 2B shows the lid 212 removed from the base 202 and shows the notches 222 along the lid's skirt 216 that improve the user's ability to capture the lid 212 when it is resting on a work surface and also makes it less likely to stick to a work surface due to the establishment of an area of induced vacuum between the lid 212 and work surface.

Figure 2C:
FIG. 2C shows an exemplary method for using the exemplary cell culture device of FIGS. 2A-2B in accordance with an embodiment of the present disclosure.
Figure 2B:
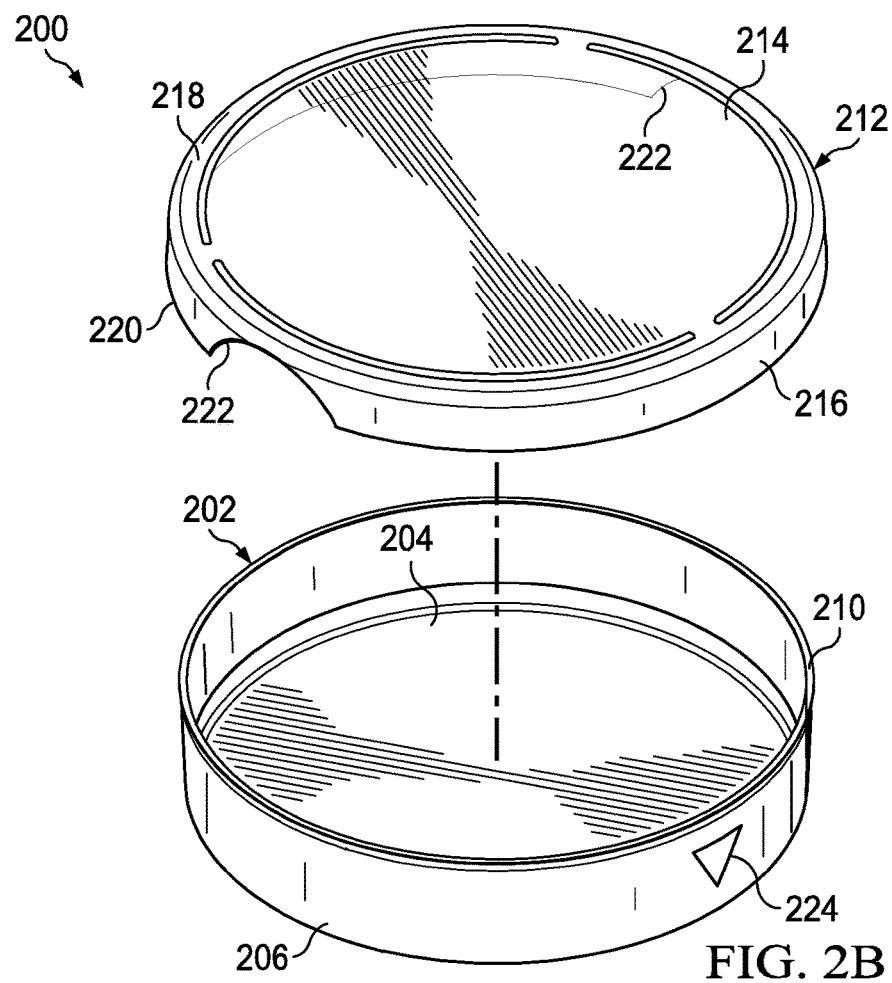
FIG. 2B shows the exemplary cell culture device of FIG. 2A with the lid removed from the base in accordance with an embodiment of the present disclosure.

Referring to FIG. 2C, there is illustrated an exemplary method 200c showing how a user could use the cell culture device 200 in accordance with an embodiment of the present disclosure. At step 202c, the user could grip the base 202 (in particular the base sidewall 206) through the notches 222 in the lid 212 when the lid 212 is fitted over the base 202. At step 204c, the user could move the gripped base 202 and the fitted lid 212 from a first location (e.g. a stack of cell culture devices 200) to a second location (e.g. a ventilated hood, a laboratory work surface, etc.). Further, the user at step 206c could remove the lid 212 from the base 202 by gripping the lid 212 at location(s) other than at the two notches 222. One skilled in the art will also readily appreciate that there are many other ways a user could use the cell culture device 200 and still be within the scope of the present disclosure (e.g. unstacking and restacking devices 200).

Figure 3A:
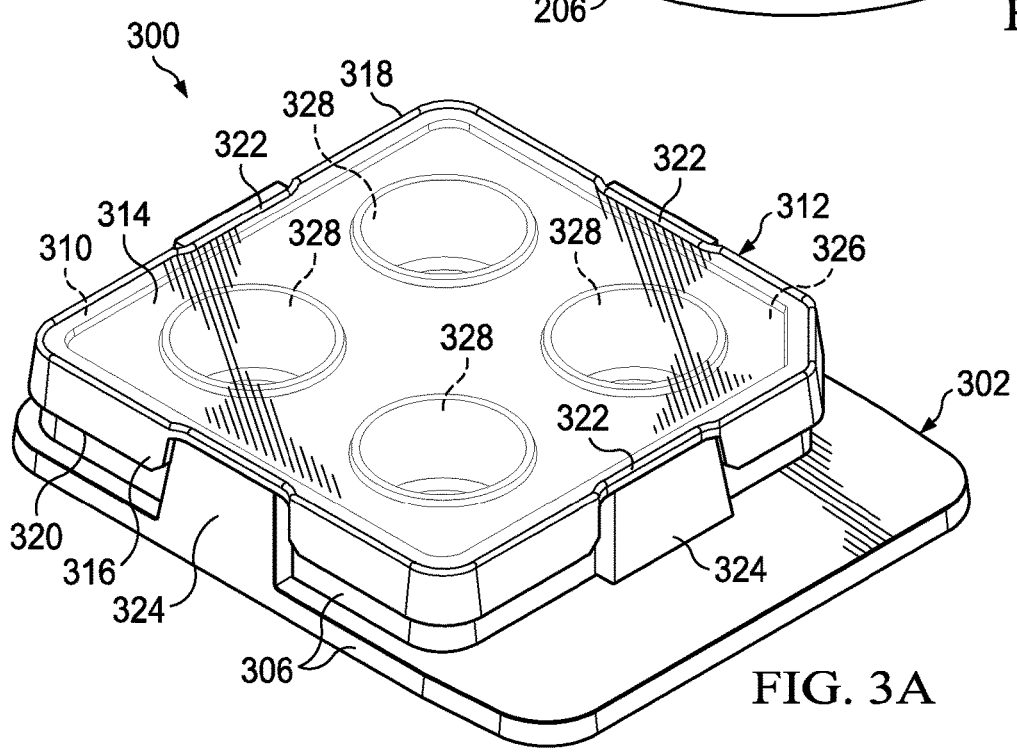
FIG. 3A shows an exemplary cell culture device having a lid with four notches (only two viewable in the image) that is fitted to a base with four gripping pads (only two viewable in the image) in accordance with an embodiment of the present disclosure.
Figure 3B:
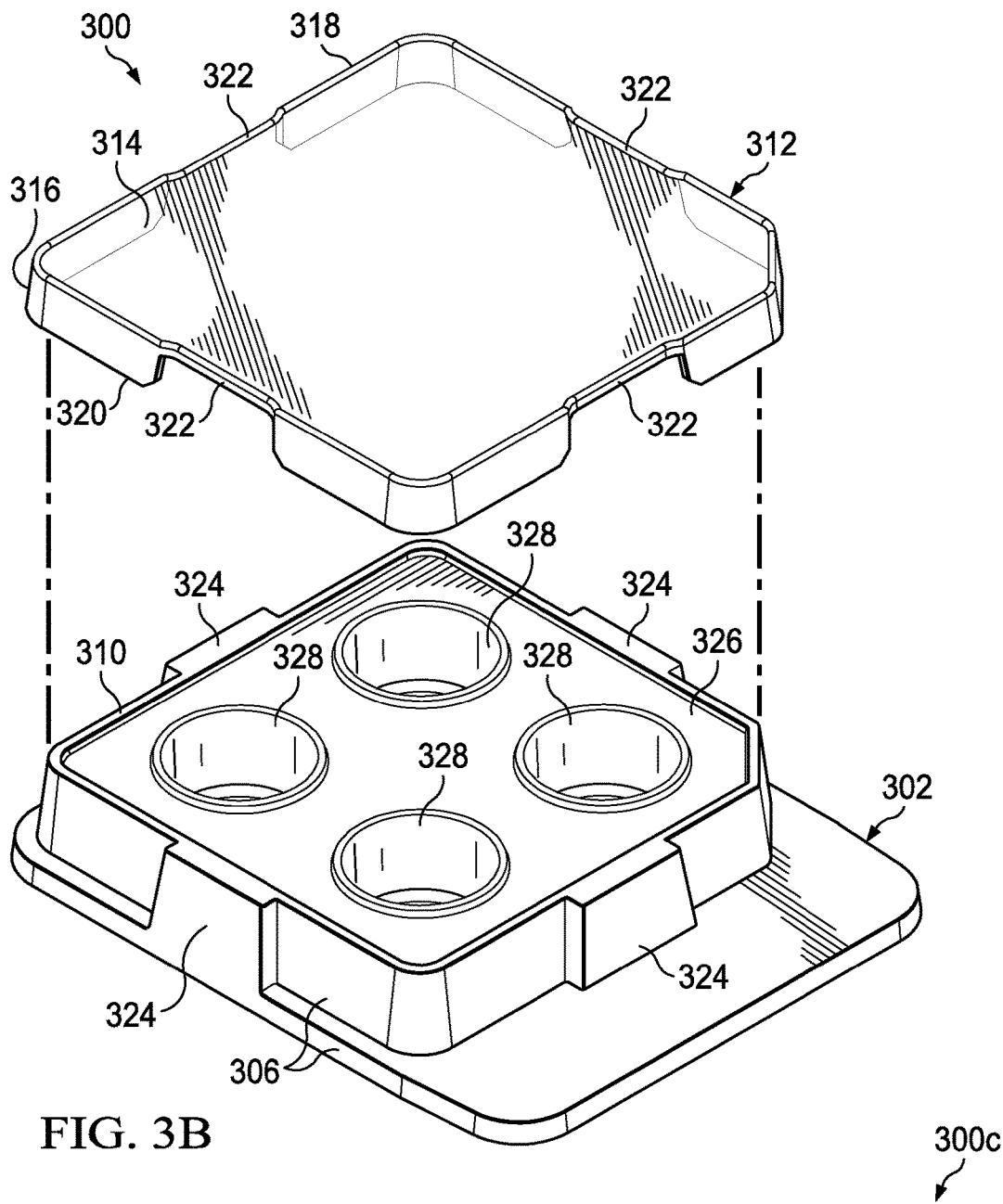
FIG. 3B shows the exemplary cell culture device of FIG. 3A with the lid removed from the base in accordance with an embodiment of the present disclosure.

Referring to FIGS. 3A-3B, there is illustrated an exemplary cell culture device 300 configured in accordance with an embodiment of the present disclosure. The cell culture device 300 (which in this example has a 4 well IVF plate configuration) comprises a base 302 having a stepped bottom skirt 306 (i.e. base sidewall 306) that has a top edge 310 that is connected to an upper panel 326 supporting multiple wells 328. The cell culture device 300 further comprises a lid 312 configured to fit over the base 302. The lid 312 has a top panel 314 and a lid sidewall 316 (i.e. skirt 316) extending downwardly from the top panel 314, where the lid sidewall 316 is connected to the top panel 314 at edge 318 and has a bottom edge 320. The lid sidewall 316 also has four notches 322 located therein, wherein each one of the notches 322 is sized to fit a human finger. In addition, the cell culture device's base sidewall 306 has four gripping pads 324 extending therefrom, where each one of the gripping pads 324 has at least a portion thereof present within a corresponding one of the notches 322 when the lid 312 is fitted over the base 302.

The exemplary cell culture device 300 shown features prominent areas referred to herein as gripping pads 324 (finger pads 324) molded into the base sidewall 306 of the base 302 and also features the lid 312 having notched out areas referred to herein as notches 322 along its skirt 316. The specific cell culture device 300 shown is a 4-Well IVF (in vitro fertilization) plate but as described above can have any number of configurations. The cell culture device 300 shown includes four gripping pads 324 and four notches 322 but designs can include more or fewer pairs of gripping pads 324 and notches 322 as desired. As detailed in FIGS. 3A-3B, the lid 312 includes four notches 322 to accommodate the presence of the four gripping pads 324 on the base 302. The lid's notches 322 provide unobscured finger and thumb access to the base's gripping pads 324 when the lid 312 and base 302 are paired. When a pair of gripping pads 324 are provided as shown on opposing sides of the base 302, the pair of gripping pads 324 provide contact areas on the base 302 for the user to pinch between their thumb and finger to enable the manipulation of the paired base 302 and lid 312. Further, the paired gripping pads 324 (on opposing sides of the base 302) in this example are located on or very near the mass centerline of the cell culture device 300 to induce the user to lift the cell culture device 300 in a manner that is less likely to tip the cell culture device 300 during manipulation. Current cell culture devices do not include gripping pads 324 such as those shown herein and instead rely on the user to pinch the skirt of the base and lid concurrently in order manipulate the paired base and lid system. As will be understood by those skilled in the art of the use of cell culture devices, the prominent gripping pads 324, when paired with a notched lid 312, provide a base and lid system that is easier to lift as a paired system when compared to the current cell culture devices. Further, as will be understood by those skilled in the art, the enhanced design of the cell culture device 300 enables the user to pick-up the paired base 302 and lid 312 by contacting the gripping pads 324 on opposing sides of the base 302, setting the cell culture device 300 down on a work surface, then shifting their finger and thumb to opposing points on the lid's skirt 316 at non-notched areas so as to deftly remove the lid 312 from the base 302 to enable pipetting or other laboratory work flow activities. Basically, the prominent gripping pads 324 provide contact points to enable the lifting of the paired lid 312 and base 302 while the lid's skirt 316 provides contact areas for manipulation of the lid 312 separate from the base 302. Further, FIG. 3B shows the lid 312 removed from the base 302 and shows the notches 322 along the lid's skirt 316 that improve the user's ability to capture the lid 312 when it is resting on a work surface and also makes the lid 312 less likely to stick to a work surface due to the establishment of an area of induced vacuum between the lid 312 and work surface. While the cell culture device 300 as shown does not include a lid skirt in the notched out areas, it is possible to include a partial skirt in this area if desired (e.g. see cell culture devices 600 and 700).

Figure 3C:
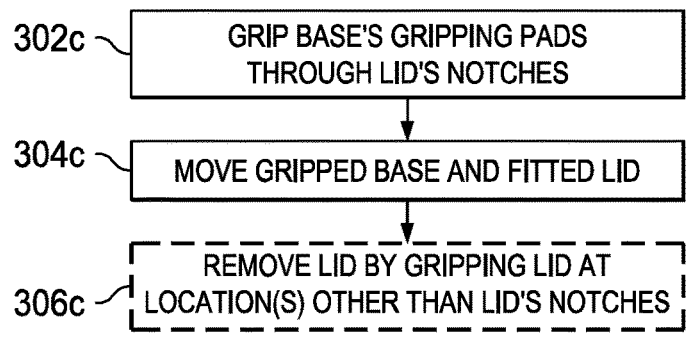
FIG. 3C shows an exemplary method for using the exemplary cell culture device of FIGS. 3A-3B in accordance with an embodiment of the present disclosure.

Referring to FIG. 3C, there is illustrated an exemplary method 300c showing how a user could use the cell culture device 300 in accordance with an embodiment of the present disclosure. At step 302c, the user could grip the gripping pads 324 through the notches 322 in the lid 312 when the lid 312 is fitted over the base 302. At step 304c, the user could move the gripped base 302 and the fitted lid 312 from a first location (e.g. a stack of cell culture devices 300) to a second location (e.g. a ventilated hood). Further, the user at step 306c could remove the lid 312 from the base 302 by gripping the lid 312 at a location other than at the two notches 322. One skilled in the art will also readily appreciate that there are many other ways a user could use the cell culture device 300 and still be within the scope of the present disclosure (e.g. unstacking and restacking devices 300).

Figure 4A:
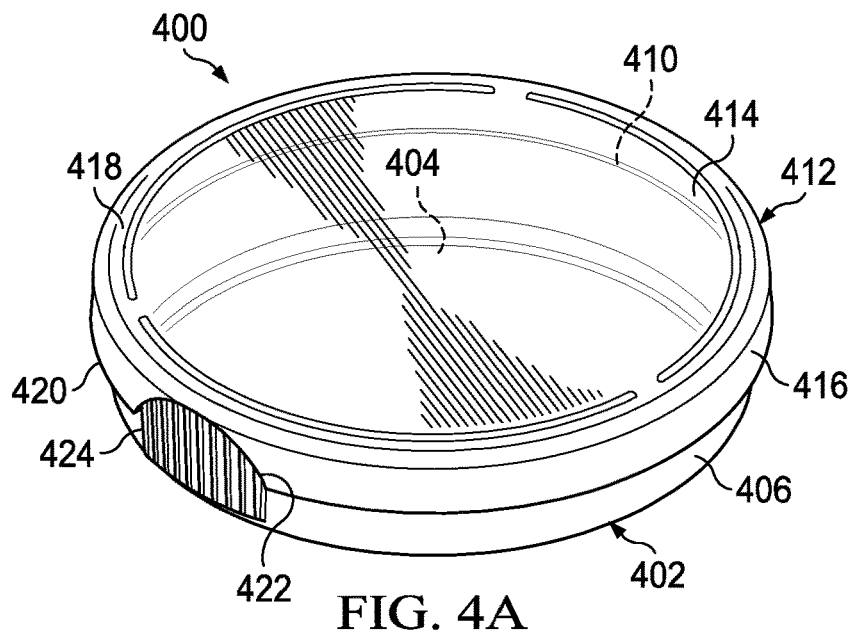
FIG. 4A shows an exemplary cell culture device having a dish base with two textured gripping pads (only one viewable in the image) that is fitted to a lid with two notches in accordance with an embodiment of the present disclosure.
Figure 4B:
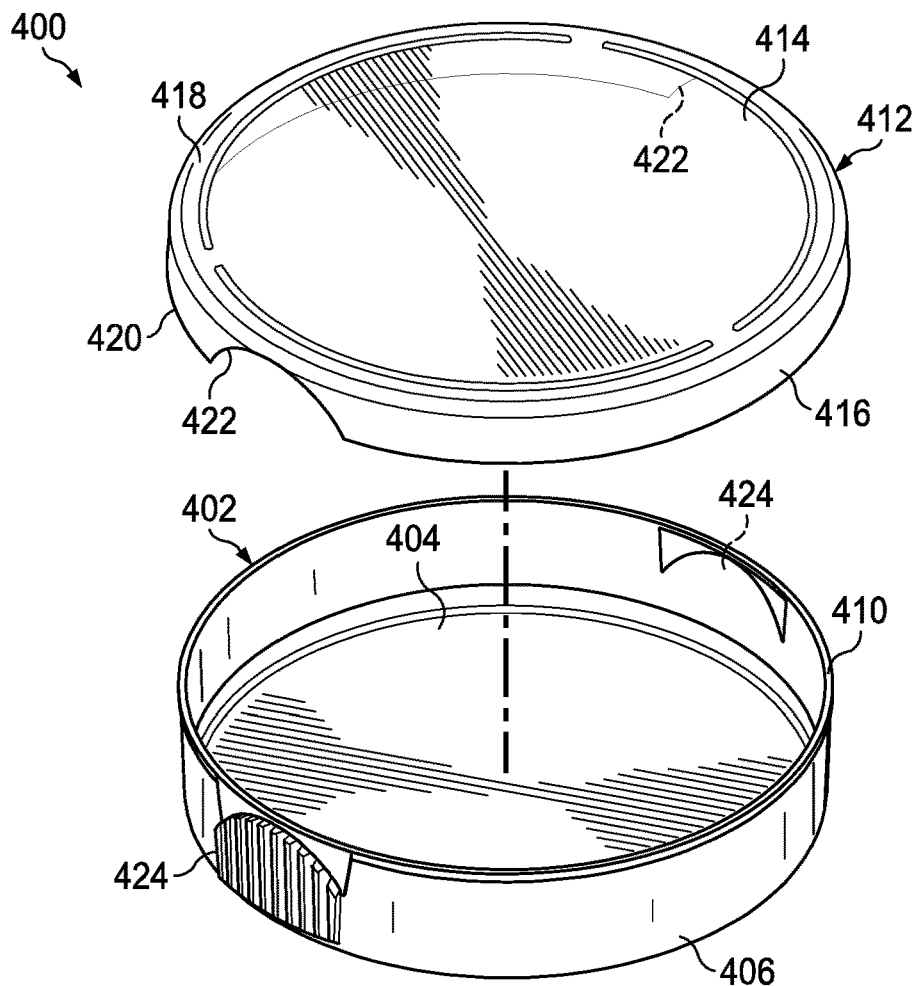
FIG. 4B shows the exemplary cell culture device of FIG. 4A with the lid removed from the base in accordance with an embodiment of the present disclosure.

Referring to FIGS. 4A-4B, there is illustrated an exemplary cell culture device 400 configured in accordance with an embodiment of the present disclosure. The cell culture device 400 (which in this example has a petri dish configuration) comprises a base 402 having a bottom panel 404 and a base sidewall 406 extending upwardly from the bottom panel 404, where the base sidewall 406 is connected to the bottom panel 404 and has top edge 410. The cell culture device 400 further comprises a lid 412 configured to fit over the base 402. The lid 412 has a top panel 414 and a lid sidewall 416 (i.e. skirt 416) extending downwardly from the top panel 414, where the lid sidewall 416 is connected to the top panel 414 at edge 418 and has a bottom edge 420. The lid sidewall 416 also has two notches 422 (more possible) located therein, wherein each one of the notches 422 is sized to fit a human finger. That is, the notches are structured to allow a user to grip the plate exposed by the notches. In addition, the cell culture device's base sidewall 406 has two gripping pads 424 (more possible) formed therein and extending therefrom (one gripping pad 424 is viewable while the other gripping pad 424 which is located on opposite side of the base sidewall 406 is not viewable). Each one of the gripping pads 424 has at least a portion thereof present within a corresponding one of the notches 422 when the lid 412 is fitted over the base 402. The notches 422 are preferably designed in round type form as shown to help enable the user to rotationally align the lid 412 on the base 402. The notches 422 in the lid 412 allow for unobscured access to the base 402 when the lid 412 and base 402 are in paired form as shown in FIG. 4A. In operation, a user could use the cell culture device 400 by gripping the gripping pads 424 through the notches 422 in the lid 412 when the lid 412 is fitted over the base 402, and moving the gripped base 402 and the fitted lid 412 from a first location (e.g. a stack of cell culture devices 400) to a second location (e.g. a ventilated hood). Further, the user may remove the lid 412 from the base 402 by gripping the lid 412 at a location other than at the two notches 422.

Figure 5:
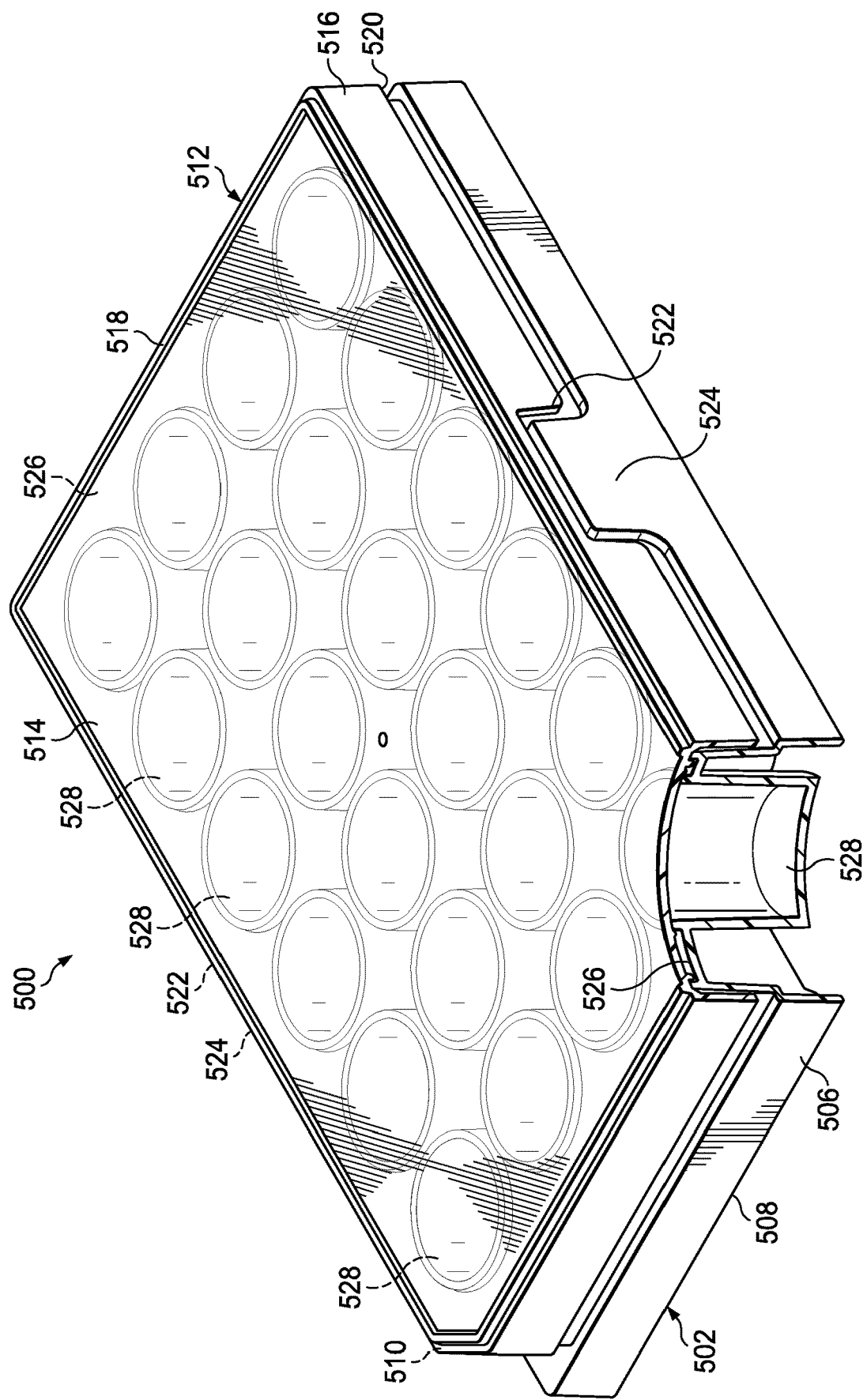
FIG. 5 shows an exemplary cell culture device having a multi-well plate base with two rectangular gripping pads (only one viewable in the image) that is fitted to a lid with two rectangular notches (only one viewable in the image) in accordance with an embodiment of the present disclosure.

Referring to FIG. 5, there is illustrated an exemplary cell culture device 500 configured in accordance with an embodiment of the present disclosure. The cell culture device 500 (which in this example has a 24 multi-well plate configuration) comprises a base 502 having a stepped bottom skirt 506 (i.e. base sidewall 506), where the bottom skirt 506 has a bottom edge 508 that is typically rested upon a work surface and has a top edge 510 that supports an upper panel 526 which supports one or more wells 528. The cell culture device 500 further comprises a lid 512 configured to fit over the base 502. The lid 512 has a top panel 514 and a lid sidewall 516 (e.g. skirt 516) extending downwardly from the top panel 514, where the lid sidewall 516 is connected to the top panel 514 at edge 518 and has a bottom edge 520. The lid sidewall 516 also has two notches 522 (more possible) located therein, wherein each one of the notches 522 (e.g. rectangular shape) is sized to fit a human finger (one notch 522 is viewable while the other notch 522 which is located on opposite side of the lid sidewall 516 is not viewable). In addition, the cell culture device's base skirt 506 (i.e. base sidewall 506) has two gripping pads 524 (more possible) formed therein and extending therefrom (one gripping pad 524 is viewable while the other gripping pad 524 which is located on the opposite side of the base sidewall 506 is not viewable). Each one of the gripping pads 524 (e.g. rectangular shape) has at least a portion thereof present within a corresponding one of the notches 522 when the lid 512 is fitted over the base 502. In operation, a user could use the cell culture device 500 by gripping the gripping pads 524 through the notches 522 in the lid 512 when the lid 512 is fitted over the base 502, and moving the gripped base 502 and the fitted lid 512 from a first location (e.g. a stack of cell culture devices 500) to a second location (e.g. a ventilated hood). Further, the user may remove the lid 512 from the base 502 by gripping the lid 512 at a location other than at the two notches 522.

Figure 6:
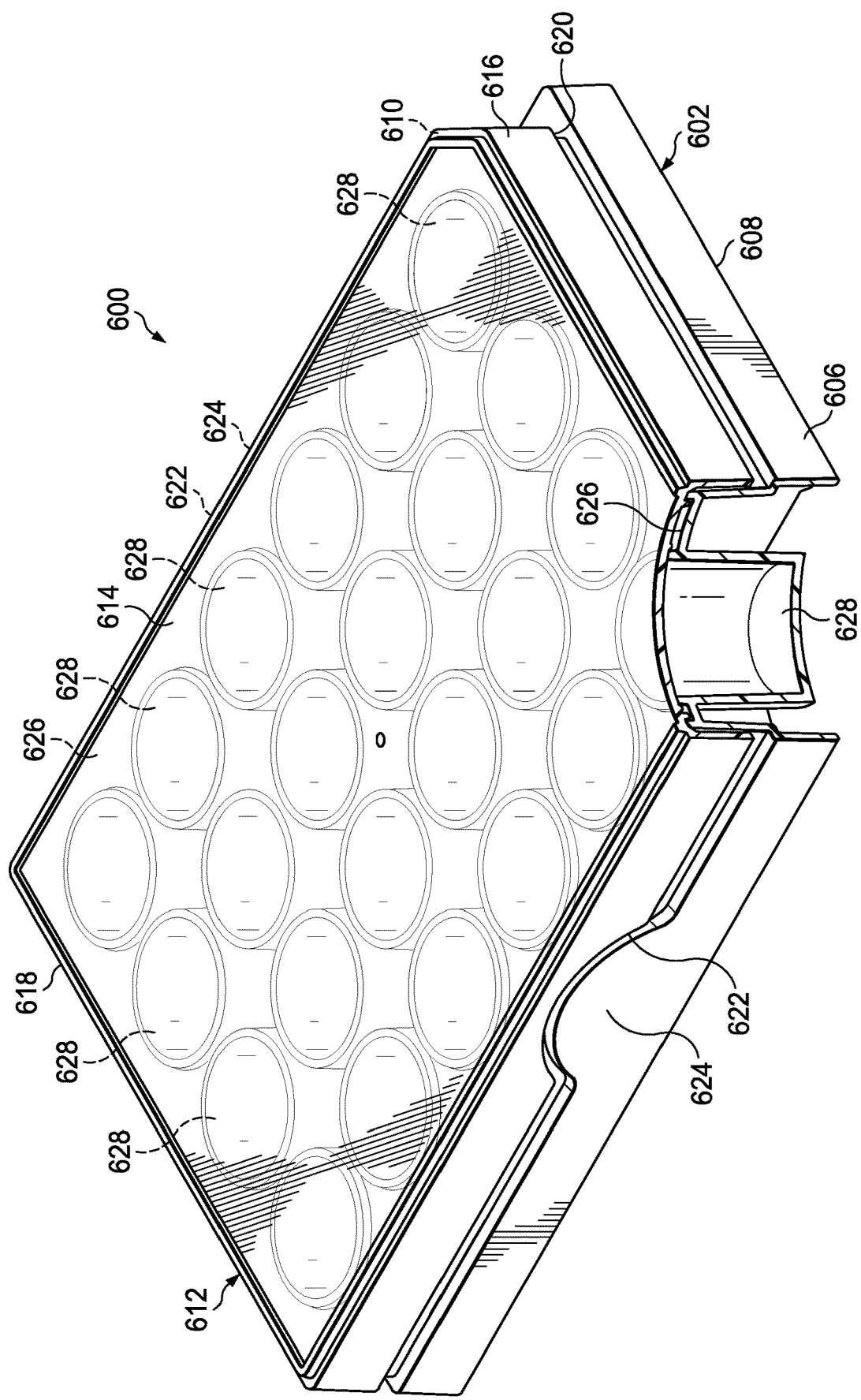
FIG. 6 shows an exemplary cell culture device having a multi-well plate base with two semi-oval gripping pads (only one viewable in the image) that is fitted to a lid with two semi-oval notches (only one viewable in the image) in accordance with an embodiment of the present disclosure.

Referring to FIG. 6, there is illustrated an exemplary cell culture device 600 configured in accordance with an embodiment of the present disclosure. The cell culture device 600 (which in this example has a 24 multi-well plate configuration) comprises a base 602 having a stepped bottom skirt 606 (i.e. base sidewall 606). where the bottom skirt 606 has a bottom edge 608 that is typically rested upon a work surface and has a top edge 610 that supports an upper panel 626 which supports one or more wells 628. The cell culture device 600 further comprises a lid 612 configured to fit over the base 602. The lid 612 has a top panel 614, and a lid sidewall 616 (i.e. skirt 616) extending downwardly from the top panel 614, where the lid sidewall 616 is connected to the top panel 614 at edge 618 and has a bottom edge 620. The lid sidewall 616 also has two notches 622 (more possible) located therein, wherein each one of the notches 622 (e.g. semi-oval shape) is sized to fit a human finger (one notch 622 is viewable while the other notch 622 which is located on the opposite side of the lid sidewall 616 is not viewable). In addition, the cell culture device's base skirt 606 (i.e. base sidewall 606) has two gripping pads 624 (more possible) formed therein and extending therefrom (one gripping pad 624 is viewable while the other gripping pad 624 which is located on the opposite side of the base sidewall 606 is not viewable). Each one of the gripping pads 624 (e.g. semi-oval shape) has at least a portion thereof present within a corresponding one of the notches 622 when the lid 612 is fitted over the base 602. As can be seen, the cell culture device 600 replicates the design approach associated with the cell culture device 500 in that there is an extension of the base skirt 606 (i.e. base sidewall 606) of the base 602 to provide the gripping pads 624, but the gripping pads 624 have a round top edge that improves the ability of the user to align the lid 612 to the base 602. Further, the cell culture device 600 has the lid 612 which is configured such that there is a partial skirt in the area just above the gripping pad 624. Providing the lid 612 with this partial skirt above the gripping pad 624 is advantageous for the cell culture device 600 that requires reduced evaporation from within the cell culturing areas of the base 602. The partial skirt on the lid 612 inhibits airflow between the lid 612 and the base 602 and therefore reduces the evaporation rate of cell culture media from within the cell culturing areas of the cell culture device 600. In operation, a user could use the cell culture device 600 by gripping the gripping pads 624 through the notches 622 in the lid 612 when the lid 612 is fitted over the base 602, and moving the gripped base 602 and the fitted lid 612 from a first location (e.g. a stack of cell culture devices 600) to a second location (e.g. a ventilated hood). Further, the user may remove the lid 612 from the base 602 by gripping the lid 612 at a location other than at the two notches 622.

Figure 7:
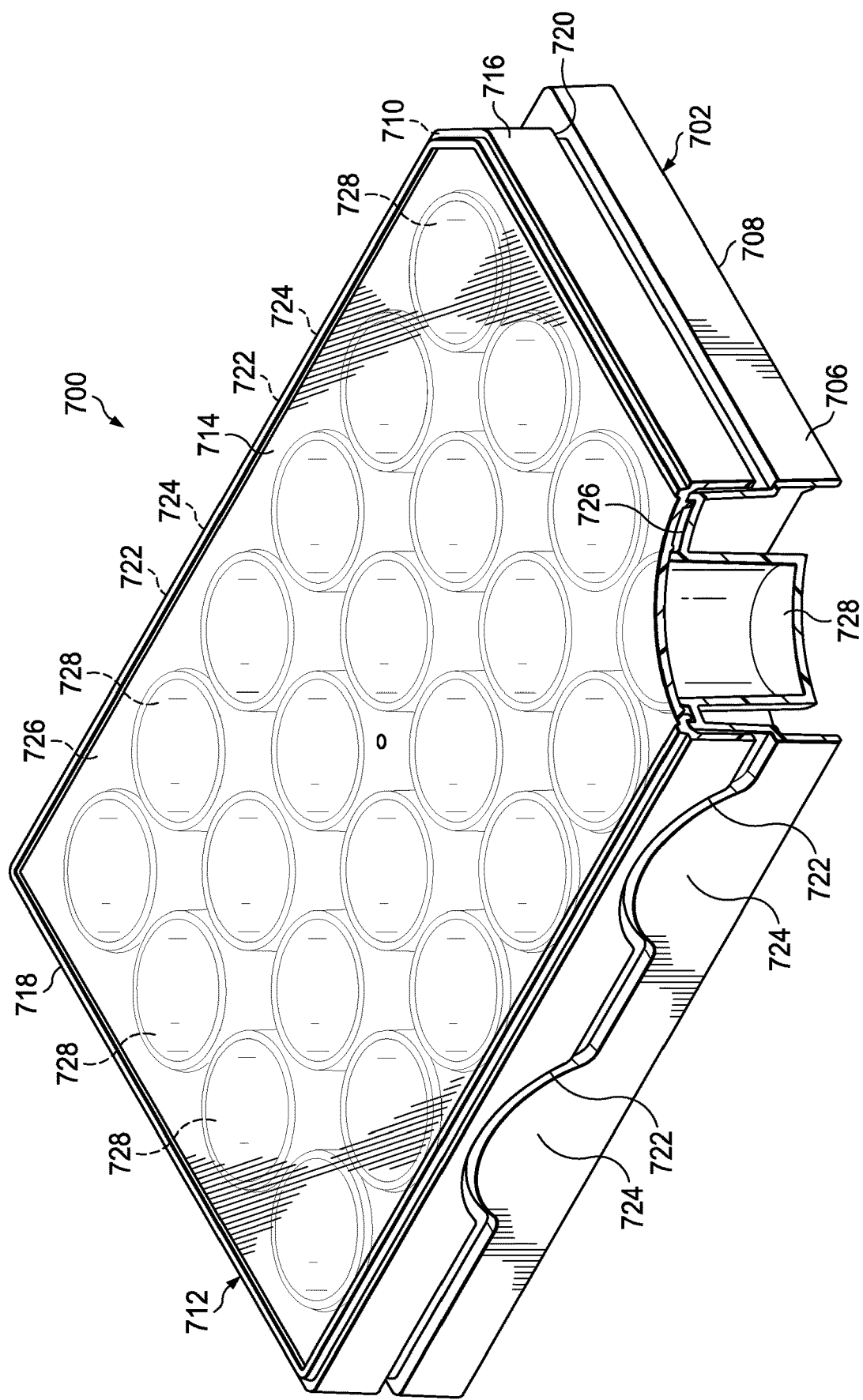
FIG. 7 shows an exemplary cell culture device having a multi-well plate base with four semi-oval gripping pads (only two viewable in the image) that is fitted to a lid with four semi-oval notches (only two viewable in the image) in accordance with an embodiment of the present disclosure.

Referring to FIG. 7, there is illustrated an exemplary cell culture device 700 configured in accordance with an embodiment of the present disclosure. The cell culture device 700 (which in this example has a 24 multi-well plate configuration) comprises a base 702 having a stepped bottom skirt 706 (i.e. base sidewall 706), where the base skirt 706 has a bottom edge 708 that is typically rested upon a work surface and a top edge 710 that supports an upper panel 726 which supports one or more wells 728. The cell culture device 700 further comprises a lid 712 configured to fit over the base 702. The lid 712 has a top panel 714, and a lid sidewall 716 (e.g. skirt 716) extending downwardly from the top panel 714, where the lid sidewall 716 is connected to the top panel 714 at edge 718 and has a bottom edge 720. The lid sidewall 716 also has four notches 722 (more possible) located therein, wherein each one of the notches 722 (e.g. semi-oval shape) is sized to fit a human finger (two notches 722 are viewable while the other two notches 722 which are located on the opposite side of the lid sidewall 716 are not viewable). In addition, the cell culture device's base skirt 706 (i.e. base sidewall 706) has four gripping pads 724 (more possible) formed therein and extending therefrom (two gripping pads 724 are viewable while the other two gripping pads 724 which are located on the opposite side of the base sidewall 706 are not viewable). Each one of the gripping pads 724 (e.g. semi-oval shape) has at least a portion thereof present within a corresponding one of the notches 722 when the lid 712 is fitted over the base 702. In operation, a user could use the cell culture device 700 by gripping one or more pairs of opposing gripping pads 724 through the respective notches 722 in the lid 712 when the lid 712 is fitted over the base 702, and moving the gripped base 702 and the fitted lid 712 from a first location (e.g. a stack of cell culture devices 700) to a second location (e.g. a ventilated hood). Further, the user may remove the lid 712 from the base 702 by gripping the lid 712 at a location other than at the two notches 722.

As discussed above, the cell culture devices 500 and 600 shown in FIGS. 5-6 have only two gripping pads 524 and 624 which are located on opposing sides of the bases 502 and 602, while the cell culture device 700 indicates that more gripping pads 724 can be added if desired and this is true for any cell culture device configured per the present disclosure. The larger dimensioned cell culture devices such as a multiple well cell culture plate may benefit by having additional pairs of gripping pads 524 and 624. For example, multiple well plates can have dimensions roughly 3 inches wide by 5 inches long by 0.5 inches tall. With a device having these dimensions it might be advantageous to provide two sets of gripping pads on each long wall as shown in FIG. 7 so that the distance from the end of the device to the first set of gripping pads is kept to about 1.5 inches to more closely match the natural reach distance from a person's thumb and middle finger to the palm of their hand.

Referring to FIGS. 8A-8B, there is illustrated an exemplary cell culture device 800 configured in accordance with an embodiment of the present disclosure. The cell culture device 800 (which in this example has a petri dish configuration) comprises a base 802 having a bottom panel 804 and a base sidewall 806 extending upwardly from the bottom panel 804, where the base sidewall 806 is connected to the bottom panel 804 and has a top edge 810. The cell culture device 800 further comprises a lid 812 configured to fit over the base 802. The lid 812 has a top panel 814 and a lid sidewall 816 (i.e. skirt 816) extending downwardly from the top panel 814, where the lid sidewall 816 is connected to the top panel 814 at edge 818 and has a bottom edge 820 (note: the lid 812 in this example is fully skirted while the lids 212, 312, 412, 512, 612 and 712 in previous examples had notches formed therein). The cell culture device's base sidewall 806 further has an outer surface 821, where the outer surface 821 has two gripping tabs 824 (more possible) extending therefrom, where each of the gripping tabs 824 have an inner side 826 where a gap 828 is present between the outer surface 821 of the base sidewall 806 and the inner side 826 of each of the gripping tabs 824, and where each of the gaps 828 is sized to receive the lid sidewall 816 when the lid 812 is fitted over the base 802. Alternatively, if desired a single gripping tab 824 (e.g. gripping rim 824) configured as discussed above could extend around the entire circumference of the base sidewall 806.

The cell culture device 800 has a different form when compared to the previous cell culture devices 200, 300, 400, 500, 600, 700 in that the cell culture device 800 has gripping tabs 824 appended to or otherwise extending from the base's sidewall 806 and also has a fully skirted lid 812. This design approach allows the user to capture only the base 802 of the lidded cell culture device 800 even when a fully skirted lid 812 is provided. This design variation includes appendages (i.e. gripping tabs 824) along the base's sidewall 806 that act as finger contact pads. Similar to the gripping pads 324 in the device design shown in FIGS. 3A-3B, the gripping tabs 824 can be molded into the base 802 to provide the user locations to place their thumb and finger to pinch and lift the base 802 and lid 812 as a paired system. The cell culture device 800 shown includes two gripping tabs 824 provided on opposing sides of the device, but additional gripping tabs could be provided (e.g. a total of 4 finger tabs) if desired. Again, the gripping tabs 824 are shown on this cell culture device 800 as being located on the mass centerline of the product to induce the user to lift the cell culture device 800 in a manner less likely to tip the cell culture device 800 during manipulation. As will be understood by those skilled in the art of the use of cell culture devices, the enhanced design of the cell culture device 800 enables the user to pick up the paired base 802 and lid 812 by contacting the gripping tabs 824 located on opposing sides of the base 802, set the cell culture device 800 down on a work surface, and then shift their finger and thumb to opposing points on the lid skirt 816 so as to remove the lid 812 from the base 802 to enable pipetting or other laboratory work flow actions. The gripping tabs 824 provide contact points to enable the lifting of the paired lid 812 and base 802 while the lid skirt 816 provides contact areas for manipulation of the lid 812 separate from the base 802.

Figure 8C:
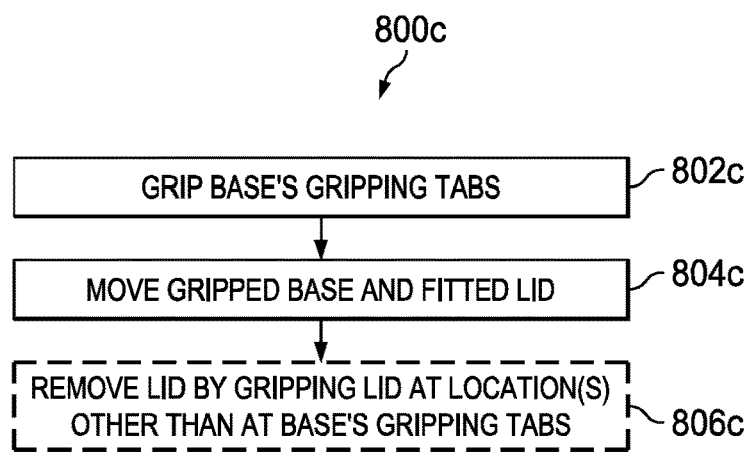
FIG. 8C shows an exemplary method for using the exemplary cell culture device of FIGS. 8A-8B in accordance with an embodiment of the present disclosure.

Referring to FIG. 8C, there is illustrated an exemplary method 800*c* showing how a user could use the cell culture device 800 in accordance with an embodiment of the present disclosure. At step 802*c*, the user could grip the gripping tabs 824 extending from the base 802 when the lid 812 is fitted over the base 802. At step 804*c*, the user could move the gripped base 802 and the fitted lid 812 from a first location (e.g. a stack of cell culture devices 800) to a second location (e.g. a ventilated hood). Further, the user at step 806*c* could remove the lid 812 from the base 802 by gripping the lid 812 at a location other than at the two gripping tabs 824. One skilled in the art will also readily appreciate that there are many other ways a user could use the cell culture device 800 and still be within the scope of the present disclosure (e.g. unstacking and restacking of devices).

A salient point in the foregoing discussion which should be appreciated is that the profile or exact design of the gripping pads 324, 424, 524, 624, 724 and gripping tabs 824 can be varied and still accomplish the device performance characteristics and desired functions. For instance, the gripping pads 324 and gripping tabs 824 can extend beyond the projected dimensions of the lid sidewall 316 (e.g. see FIG. 3A). Alternatively, the gripping pads 424, 524, 624, 724 can be flush with the outer surface of the lid sidewall 412, 512, 612, 712 (e.g. see FIGS. 4, 5, 6 and 7). The gripping pads 324, 424, 524, 624, 724 and gripping tabs 824 can be designed as being generally rectangular (e.g. see FIGS. 3, 5 and 8), rounded or semi-oval (e.g. see FIGS. 4, 6 and 7) or any other desired shape to help with lid-to-base alignment or to provide distinguishing styling to the cell culture device. The surface texture of the gripping pads 324, 424, 524, 624, 724 and gripping tabs 824 can be varied to provide improved gripping performance, tactile feedback to the user or to provide distinguishing styling to the cell culture device.

Each base 202, 302, 402, 502, 602, 702, 802 and lid 212, 312, 412, 512, 612, 712, 812 may be manufactured by any suitable manufacturing method and may be formed as a single piece or an assembly of separate pieces. In some embodiments, the base 202, 302, 402, 502, 602, 702, 802 is manufactured as a single piece, including the gripping pads 324, 424, 524, 624, 724 or gripping tabs 824, by injection molding. Likewise, in some embodiments, the lid 212, 312, 412, 512, 612, 712, 812 is manufactured as a single piece by injection molding. In some embodiments, the base 202, 302, 402, 502, 602, 702, 802 and/or lid 212, 312, 412, 512, 612, 712, 812 is manufactured by 3-dimensional printing. Any suitable material may be used in the fabrication of the cell culture devices 200, 300, 400, 500, 600, 700, 800. In some embodiments, the base 202, 302, 402, 502, 602, 702, 802 and/or lid 212, 312, 412, 512, 612, 712, 812 is composed of a thermoplastic resin (e.g. polystyrene, polypropylene, cyclic olefin copolymer, etc). In some embodiments, the base 202, 302, 402, 502, 602, 702, 802 and/or lid 212, 312, 412, 512, 612, 712, 812 is composed of glass or combinations of glass and polymer. In some embodiments, the base 202, 302, 402, 502, 602, 702, 802 and/or lid 212, 312, 412, 512, 612, 712, 812 are made from a metal or ceramic.

The cell culture device 200, 300, 400, 500, 600, 700, 800 may be any desired shape or form. In some embodiments, the cell culture devices are configured as a dish (e.g. a petri dish as shown as 200, 400, and 800). In some embodiments, the cell culture device are configured as a plate (e.g. an in vitro fertilization plate or multi-well plate as shown as 300, 500, 600, and 700). In some embodiments, the base 202, 402, 802 and lid 212, 412, 812 are circular in shape (e.g. circle, oval, etc.). In some embodiments, the base 302, 502, 602, 702 and lid 312, 512, 612, 712 are polygonal in shape (e.g. square, rectangular, etc.).

In some embodiments, the gripping pads 324, 424, 524, 624, 724 or gripping tabs 824 are textured, for example, with grooves or dots or any other textured pattern that enhances the grip of a user to the gripping pads 324, 424, 524, 624, 724 or gripping tabs 824 (e.g. when a user has gloved hands, wet hands, etc.) or provides tactile feedback that the user has made proper and sufficient contact with the gripping areas of the cell culture device 200, 300, 400, 500, 600, 700, 800. Any number of gripping pads 324, 424, 524, 624, 724 or gripping tabs 824 may be employed. In some embodiments, two gripping pads 424, 524, 624 or two gripping tabs 824 are provided; see FIGS. 4-6 and 8. In some embodiments four gripping pads 324, 724 are provided; see FIGS. 3 and 7. As shown herein, two of the gripping pads 324, 424, 524, 624, 724 or gripping tabs 824 are arranged on opposite sides of the base 302, 402, 502, 602, 702, 802 from each other to allow a pinching action to pick up the cell culture device 300, 400, 500, 600, 700, 800. In some embodiments, the two gripping pads 324, 424, 524, 624, 724 or gripping tabs 824 are located along a mass centerline of the base 302, 402, 502, 602, 702, 802. In one embodiment such as the cell culture device 200 the placement of the notched lid 812 on the base 802 defines the gripping regions. For example, on a circular cell culture device 200 as shown in FIGS. 2A-2B where the lid 202 has notches 222, the position of the lid 812 on the base 802 can define the gripping regions at any point around the circumference of the base 802.

The well designs of the cell culture device 200, 300, 400, 500, 600, 700, 800 may be of any type useful for cell culture. In some embodiments, one or more surfaces (e.g., the bottom panel 204, 404 or bottom of well 328, 528, 628, 728 of the base 202, 302, 402, 502, 602, 702, 802 and/or the interior of the base sidewall 206, 406, 806 or interior sidewall of wells 328, 528, 628, 728) may be coated, treated, or textured to promote cell culture of particular types of cells. In some embodiments the bottom panel 204, 404, 804 or bottom of the wells 328, 528, 628, 728 is flat, round, V-shaped, or provided with a sidewall to a bottom flat panel interface that is chamfered or radiused. In some embodiments, the base 202, 302, 402, 502, 602, 702, 802 is partitioned into multiple different zones or regions (i.e. a "multi-well" dish or plate). In some embodiments, markings are provided on the base 202, 302, 402, 502, 602, 702, 802 and/or lid 212, 312, 412, 512, 612, 712, 812 to enhance their functionality. For example, the base panel 204, 404, 804 may have markings that define zones that assist in cell counting or the base sidewall 206, 406, 806 or sidewall of wells 328, 528, 628, 728 may have marking that identify liquid volume in the base 202, 302, 402, 502, 602, 702, 802. For example, the triangular markings 224 and 830 on the base sidewall 206 and 806 as shown in FIGS. 2A-2B and 8A-8B are provided to show the 12 o'clock position on the cell culture device 200 and 800 to allow the user to reference specific locations around the circumference of the cell culture device 200 and 800. In some embodiments, the bottom of the base 202, 302, 402, 502, 602, 702, 802 and/or the top of the lid 212, 312, 412, 512, 612, 712, 812 can include one or more features that facilitate stable stacking of multiple cell culture devices 200, 300, 400, 500, 600, 700, 800 on top of one another.

Further provided herein are methods of culturing cells using any of the cell culture devices 200, 300, 400, 500, 600, 700, 800 described herein. In some embodiments, the method comprises culturing or otherwise manipulating a cell (e.g. oocyte, egg, sperm, primary culture, stem cell, immortalized cell, etc.) in any of the cell culture devices 200, 300, 400, 500, 600, 700, 800 described herein. In some embodiments, the method further comprises moving the cell culture device 200, 300, 400, 500, 600, 700, 800 by gripping the one or more gripping regions and moving the cell culture device 200, 300, 400, 500, 600, 700, 800 from a first location (e.g. a stack of devices, a ventilation hood, an incubator, a first region of a workspace, etc.) to a second, different location. In some embodiments, the method further comprises the step of removing the lid 212, 312, 412, 512, 612, 712, 812 from the base 202, 302, 402, 502, 602, 702, 802 by gripping the lid 212, 312, 412, 512, 612, 712, 812 at a location other than the one or more gripping regions in order to remove or add media, culturing reagents, trypsin, cells, etc. In some embodiments, the cell culture device 200, 300, 400, 500, 600, 700, 800 has preferential base lifting locations to lift the base 202, 302, 402, 502, 602, 702, 802 and lid 212, 312, 412, 512, 612, 712, 812 as a paired set (e.g. gripping regions) and preferential lid lifting locations (e.g. locations other than the base gripping regions) to lift lid 212, 312, 412, 512, 612, 712, 812 and not the base 202, 302, 402, 502, 602, 702, 802.

One skilled in the art will readily appreciate that disclosed herein are various cell culture devices 200, 300, 400, 500, 600, 700, 800 that are configured such as multiple well and microwell plates, petri dishes, in vitro fertilization dishes and in vitro fertilization plates. In particular, disclosed herein are cell culture devices 200, 300, 400, 500, 600, 700, 800 configured to minimize or eliminate the need for the user to contact the lid 212, 312, 412, 512, 612, 712, 812 when attempting to lift or move the respective lidded cell culture device 200, 300, 400, 500, 600, 700, 800. This ability to lift a lidded cell culture device 200, 300, 400, 500, 600, 700, 800 easily is an especially important design feature given the confined spaces that often exist within laboratory environments such as incubation ovens, laminar flow hoods, and cramped laboratory bench tops. The following is a discussion about some additional technical features and various advantages associated with the cell culture devices 200, 300, 400, 500, 600, 700, 800 configured in accordance with the present disclosure:

- Lidded cell culture devices which enable the user to manually lift both the lid and base as an assembly typically using the thumb and finger pinching action of one hand.
- Lidded cell culture devices that dramatically improve the user's ability to lift the base and lid concurrently.
- Lidded cell culture devices that obviate the need for the user to separate a lid from its paired base in order to move the paired lid and base.
- Lidded cell culture devices that dramatically improve the ability of the user to stack and unstack like cell culture devices by allowing the user to consistently and quickly select paired bases and lids.
- Lidded cell culture devices that improve the user's ability to adroitly remove the top cell culture device from a stack of like cell culture devices thus improving efficiency in device handling.
- Lidded cell culture devices that are easier to stack like-on-like due to the user's improved ability to handle the devices as lid and base pairs as a result of the disclosed device enhancements.
- Lidded cell culture devices that reduce the likelihood that paired bases and lids are inadvertently separated one from the other because the cell culture device designs allow the user to lift paired bases and lids concurrently.

Lidded cell culture devices which reduce the frequency that the cell culture device surfaces and wells (i.e. the cell culturing area) are exposed to the open environment thereby reducing the potential for contamination of these areas by contaminating particulate or microorganisms within the working environment (e.g. the laboratory, laminar flow hood, incubator interior space).

Lidded cell culture devices that eliminate the need for the user to pinch over the lid skirt to obtain finger and thumb capture of the base for lifting of the paired lid and base.

Lidded cell culture devices with proud finger contact gripping pads or tabs along the base wall to allow the user to capture only the base of the lidded device.

Lidded cell culture devices that incorporate lids with notched out features to account for finger contact gripping pads provided to the base wall or simply to expose the base wall to allow the user to pinch the base so as to readily pick up the base and lid as a pair.

Lidded cell culture devices with finger gripping tabs appended to the base wall to allow the user to capture only the base of the lidded device.

Lidded cell culture devices that improve the ability of the user to manipulate the cell culture device with one hand while completing other tasks with their opposite hand.

Lidded cell culture devices that reduce the propensity of the user to be required to place the lid of the cell culture device on a work surface during the cell culturing workflow.

Lidded cell culture devices with lid designs that improve the user's ability to pick up the lid from a horizontal work surface.

Lidded cell culture devices with lid designs that dramatically reduce the likelihood that the lid will stick to a horizontal work surface because the notched out area along the lid skirt allows air pressure exchange between the space under the lid and the area above and around the lid.

Lidded cell culture devices with finger contact gripping tabs provided integral to the device base that provide pinching capture points beyond the boundaries of a fully skirted lid.

Lidded cell culture device designs that induce the user to lift the cell culture device from its mass center of gravity to reduce the likelihood of tipping the cell culture device during manipulation and thereby reduce the propensity of the user to spill media or other cell culture device contents (e.g. cells).

Lidded cell culture device designs that enable the total height profile of the device to be reduced because the lid skirt height does not impact the user's ability to reach a lower portion of the base side wall for lifting of a paired base and lid.

Lidded cell culture device designs that better enable loading and removing from currently available top loading in vitro fertilization incubators. Top loading in vitro fertilization incubators typically include individual chambers with narrow side spaces surrounding the IVF plate or dish and require the user to access the IVF plate or dish from above for loading and unloading of each incubator chamber. In this condition, the user cannot easily access the IVF plate or dish base to pick the lidded device out of the incubatory chamber. By design, the addition of gripping pads or gripping tabs improves the user's ability to lift a lidded cell culture device from a confined top loading chamber such as those in currently available in vitro fertilization incubators. As a result, the designs provided in this disclosure reduce the risk that the user might spill the device contents during movement of the lidded cell culture device into and out of these top loading style incubators.

Lidded cell culture devices that allow easier and concurrent lifting of paired lids and bases.

Lidded cell culture devices that virtually eliminate the probability that the user inadvertently removes the lid from the base during device handling.

Lidded cell culture devices that are easier for the user to stack and unstack because they are more readily handled as lid and base pairs.

Lidded cell culture devices that, due to their design features, reduce the likelihood that the user is required to remove the device lid in order to transfer the device from one place to another.

Lidded cell culture devices that, due to their design features, experiences fewer occurrences of contamination to the cell culturing area.

Lidded cell culture devices that include finger gripping pads or finger gripping tabs located along the mass centerline of the devices to induce the user to lift the devices in a manner less likely to tip during manipulation.

Lidded cell culture devices with specific areas designed into the devices at which the user is to place their finger and thumb to pinch and lift the device.

Lidded cell culture devices which provide locations on the base wall that are not obscured by the lid skirt to provide robust and direct contact by the users thumb and finger to the base wall to improve the user's ability to manipulate the device as a base and lid pair.

Lidded cell culture devices that allow the user to deftly pick a lid and base pair from the top of a stack of like devices using the product's base finger gripping pads or gripping tabs, place the device on the work surface, then switch their finger and thumb position to contact the lid only so as to remove the lid and pipet media, etc. into or out of the base.

Lidded cell culture devices that improve the user's ability to handle a cell culture device with one hand while holding onto a pipettor with their other hand so as to speed laboratory operational efficiency and reduce handling mishaps.

Lidded cell culture devices with lid designs that are easier to lift from a work surface as a result of the inclusion of notched areas along the lid skirt.

Lidded cell culture devices with lid designs that are less likely to stick to a work surface due to the establishment of an area of induced vacuum between the lid and work surface. The inclusion of lid skirt notches in the proposed design allows the maintenance of a pressure equilibrium below and around the notched lid when it is placed on a work surface.

Lidded cell culture devices that include a fully skirted lid design but enable the user to have robust and direct contact to the base of the device to allow manipulation of the lidded device as a base and lid pair.

Lidded cell culture devices that help the user naturally pick up the part from its mass centerline thereby reducing the likelihood that the user will spill the devices contents.

Lidded cell culture device designs that allow for the potential to reduce the overall height of the product thereby reducing the total materials used in the product.

Lidded cell culture devices which are configured to provide improved ease of use of the devices within the laboratory environment and reduced risk that the user or robotic systems may drop the devices during handling.

As it is necessary to frequently move cell culture devices within the laboratory environment during the cell culturing process what is required and what is provided by the present disclosure are cell culture devices that are specifically designed to allow the user to pick up the lidded cell culture device from a work surface, or stack of like devices, with very little or no contact with the device lid. Such designs allow the user to engage predominantly, or only, the base of the lidded device while using a pinching action of a thumb and finger to lift the lidded cell culture device from a work surface, from within an incubator, or from a stack of similar cell culture devices. The design and general utility of the cell culture devices also allows for improved ease of use of the devices within the laboratory environment. Alterations to the disclosed designs may be conceived and implemented but are still considered to be within the scope of the present disclosure. Further, the general utility of the proposed lidded cell culture device designs that minimize or eliminate the need for the user (or robotic system) to contact the lid when attempting to lift the lidded device is a marked improvement over the state-of-the-art. The ability to lift the lidded cell culture device easily is an especially important design feature given the frequency that cell culture device are moved during cell culture workflow in a laboratory and also given the confined spaces that the user (or robotic system) typically encounters in the laboratory environment, such as incubation ovens, laminar flow hoods, and cramped laboratory bench tops.

The present disclosure provides an improvement to existing cell culture plates and dishes through design enhancements that result in improved product functionality. The disclosed cell culture devices and equivalents thereof improve the user's ability to move the devices within the laboratory environment without the need to separate the lid from the base. The designs of the new cell culture devices are an improvement over current designs because they improve the ease of use of the devices, improve laboratory efficiency by simplifying cell culturing workflow, and reduce the potential for the introduction of contaminants to the cell culturing area of the devices. The improvement to the cell culture devices is accomplished through the addition of notches to the lid alone, through the addition of finger gripping pads to the base paired with modification to the lid skirt design (i.e. the addition of notches to the lid), or through the addition of finger gripping tabs to the side walls of the device base.

The cell culture devices described herein include a base and/or lid with special design features that allow the user to more readily pick up the devices as a paired system while still providing the user the ability to easily remove the device lid by itself.

The cell culture devices described herein can be manufactured from thermoplastic resins (e.g. clear polystyrene) using injection molding equipment and molds. One skilled in the art of plastic injection molding would be able to produce the new cell culture devices through the design and fabrication of molds for the desired cell culture devices and the development of injection molding processes and techniques to produce the desired cell culture devices.

Currently manufactured cell culture dishes (e.g. petri dishes and in vitro fertilization dishes) include a lid with a full skirt that has a greater diameter than the outside diameter of the base (i.e. the dish) sidewalls. The purpose of the lid is to cover the dish to protect its contents from contamination from the surrounding environment. Additionally, the lid acts to allow controlled gas exchange between the area enclosed within the dish and lid and the environment surrounding the dish and lid. For dishes containing media, the lid acts to reduce media evaporation. The full skirt of the lid extends downward around the entire circumference of the dish side walls and, in doing so, prohibits easy access of the users thumb and fingers to the side walls to allow the user to readily pinch or grasp the base (i.e. dish) to lift and transport the dish and lid as a paired set. The new cell culture devices described herein address this problem and other problems.

Currently manufactured cell culture plates (e.g. multiwell plates, IVF plates) include lids with full skirts that have greater width and length dimensions than those of their respective base sidewalls. The purpose of the lid is to cover the plate to protect its contents from contamination from the surrounding environment. Additionally, the lid acts to allow controlled gas exchange between the area enclosed within the plate and lid and the environment surrounding the plate and lid. For plate wells containing media, the lid acts to reduce media evaporation. The full skirt of the lid extends downward over the base sidewalls and, in doing so, prohibits easy access of the users thumb and fingers to the base sidewalls to allow the user to readily pinch or grasp the base (i.e. plate) to lift and transport the plate and lid as a paired set. The new cell culture devices described herein address this problem and other problems.

The new cell culture devices are a novel solution to a functional issue inherent in the design of currently available cell culture devices, namely, the inability of the user to easily pick up the devices as base and lid pairs (i.e. with the lid mated with its base). The new cell culture device designs enable the user to more easily lift the cell culture plates and dishes by providing either notched lids alone, notched lids paired with corresponding gripping pads on their bases, or gripping tabs included on their bases while still providing lid sidewall areas which can be used as preferential locations to manipulate the lid by itself. The present disclosure provides a solution to the user's need to be able to more easily manipulate and transfer lidded cell culture devices within the laboratory environment while still providing easy manipulation and removal of the lid from the base. The ability to more easily manipulate the lid and base of the cell culture device as a pair will result in less likelihood that the contents of the cell culture device be spilled due to mishandling and less likelihood that the contents of the cell culture device be contaminated due to unnecessary removal of the lid from the base.

An embodiment of the present disclosure is shown in FIGS. 3A-3B where the cell culture device includes finger gripping pads molded into the side walls of the base and sections of the lid skirt have been notched out to account for the presence of the finger gripping pads on the device base. The finger gripping pads on the side walls of the base provide locations at which the user can pinch the base between their thumb and finger to easily manipulate and transfer the lidded cell culture device. Notched out areas have been provided on the lid to accommodate the finger gripping pads provided on the base, however skirt areas have been provided on the lid to provide locations on the lid to allow the user to easily pinch and lift the lid from the base as well as to provide skirt areas required to enable the alignment and capture of the lid over the base. This embodiment can be realized for both cell culture plates and dishes.

The embodiment of cell culture device depicted in FIGS. 4A-4B is similar in nature to that of the cell culture device shown in FIGS. 3A-3B wherein finger gripping pads are provided.

The embodiments of the cell culture devices depicted in FIGS. 5-6 are provided to show that a variety of finger gripping pad shapes and profiles are possible in accordance with the present disclosure.

The embodiment of the cell culture device depicted in FIG. 7 is provided to show that the design can include a multiplicity of finger gripping pads along each of the side walls of the base of any device and that such designs are alternate embodiments of the present disclosure.

A different embodiment of the present disclosure is shown in FIGS. 8A-8B where the cell culture device has finger gripping tabs appended to the base and the lid is not required to have notched out areas. While this design approach enables the lid of the device to be fully skirted, the alignment of the lid into the space between the finger tabs and the side walls of the base in order to engage the lid over the base may be difficult to accomplish. The cell culture device depicted in FIGS. 8A-8B could be modified to reduce the height of the finger pads to minimize or eliminate this lid-to-base alignment issue. It should also be noted, however, that the amount of plastic resin required to realize this embodiment is greater than that required by a standard petri dish design or the design depicted in FIGS. 4A-4B and is more difficult to mold.

Another embodiment of the cell culture device is depicted in FIGS. 2A-2B to show that areas intended as the location to pinch the base between the user's thumb and finger can be provided by simply notching out portions of the lid skirt. While this design approach is not as elegant as the cell culture devices shown in FIGS. 3-8 wherein finger gripping pads or finger gripping tabs are established by protrusions from the base side wall or base skirt of the devices, the design approach of simply exposing portions of the side wall or skirt of the device base by providing a notched lid skirt is an alternate embodiment of the present disclosure.

The designs provided herein allow the user to deftly pick a lid and base pair from the top of a stack of like devices using one hand's digits to pinch the devices' base finger gripping pads or finger gripping tabs, place the device on a work surface, then switch their finger and thumb positions to contact the lid only so as to remove the lid and then pipet media into the base using their opposite hand. The designs thereby improve the user's ability to handle a cell culture device with one hand while holding onto a pipettor with their other hand so as to speed laboratory workflows and reduce handling mishaps.

The designs provided herein allow the user to deftly pick a lid and base pair from within a top loading incubator using one hand's digits to pinch the device's base finger gripping pads or finger gripping tabs, place the device on a work surface, then switch their finger and thumb positions to contact the lid only so as to remove the lid and then perform pipetting of embryos using their opposite hand. The designs thereby improve the user's ability to handle the cell culture device with one hand while holding onto a pipettor with their other hand so as to improve laboratory operational efficiency and reduce handling mishaps.

In some embodiments, the new cell culture devices include finger gripping pads or finger gripping tabs to provide areas on the device base specifically designated as points at which the user can pinch the device between a thumb and finger to enable lifting the device base and lid as a pair. In some such embodiments, the finger gripping pads are provided on the side walls or skirts of the base and the presence of these finger pads is accommodated by the provision of areas of reduced skirt height (e.g. notches) on the lid. In another embodiment, finger gripping tabs are appended to the base. The design features are especially important in providing improved laboratory workstream efficiencies and ergonomic benefits to the user though enhanced ease of manipulation of the base and lid as a pair while still allowing for selected manipulation of the lid separate from the base.

The designs described herein may be used to modify existing commercial products and prior designs. It may also be applied to any new, future designs. As such, cell culture devices (plates and dishes) may be manufactured using known materials and manufacturing processes.

The designs of the present disclosure may be applied to cell culture devices that include, but are not limited to, petri dishes, IVF plates, multiwell plates (e.g., 4-well, 6-well, 8-well, 12-well, 16-well, 24-well, 48-well, 96-well, 384-well, 1536-well, etc.), spheroid plates (CORNING), TRANSWELL devices (CORNING), minitrays, strips, etc.

The designs of the present disclosure are not limited by the mechanism or manner in which in the gripping regions are provided. In some embodiments, gripping regions on the base are made available by the use of notches in the lid (e.g. see FIGS. 2-7). In some such embodiments, the area under the lid's notch, when the lid is fitted on the base, exposes regions such as gripping pads of the base sidewall for direct contact to grip (e.g. by fingers, robot, etc.) the device by the base sidewall (in some cases the sidewall is in the form of a skirt) (see FIGS. 3-7). The gripping pads or gripping tabs may extend outwardly from the base sidewall (e.g. base skirt) a distance such that it extends to or beyond the projected dimensions of the lid sidewall. In other such embodiments, the lid sidewall has one or more notches such that an area of the base sidewall positioned under the notches, when the lid is fitted over said base, forms the one or more gripping regions (e.g. see FIGS. 2A-2B). In this case, the gripping regions are the regions of the base exposed by the lid's notches. In all cases, the dimensions of the new cell culture devices are selected for the intended end use functionality of the particular cell culture device.

It will be appreciated that the various disclosed embodiments may involve particular features, elements or steps that are described in connection with that particular embodiment. It will also be appreciated that a particular feature, element or step, although described in relation to one particular embodiment, may be interchanged or combined with alternate embodiments in various non-illustrated combinations or permutations.

It is also to be understood that, as used herein the terms "the," "a," or "an," mean "at least one," and should not be limited to "only one" unless explicitly indicated to the contrary. Thus, for example, reference to "an opening" includes examples having two or more such "openings" unless the context clearly indicates otherwise.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All numerical values expressed herein are to be interpreted as including "about," whether or not so stated, unless expressly indicated otherwise. It is further understood, however, that each numerical value recited is precisely contemplated as well, regardless of whether it is expressed as "about" that value. Thus, "a dimension less than 10 mm" and "a dimension less than about 10 mm" both include embodiments of "a dimension less than about 10 mm" as well as "a dimension less than 10 mm."

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method comprising A+B+C include embodiments where a method consists of A+B+C, and embodiments where a method consists essentially of A+B+C.

Although multiple embodiments of the present disclosure have been illustrated in the accompanying Drawings and described in the foregoing Detailed Description, it should be understood that the disclosure is not limited to the disclosed embodiments, but is capable of numerous rearrangements, modifications and substitutions without departing from the disclosure as set forth and defined by the following claims.

The invention claimed is:

1. A cell culture device comprising:
   a base comprising a base sidewall; and
   a lid configured to fit over the base, the lid comprising:
      a top panel; and
      a lid sidewall extending downwardly from the top panel, wherein the lid sidewall is connected to the top panel and has a bottom edge; and
      the base sidewall further has a straight outer wall, wherein the straight outer wall has at least two gripping tabs extending therefrom, wherein each of the at least two gripping tabs have a straight inner side where a gap is present between the straight outer wall of the base sidewall and the straight inner side of each of the at least two gripping tabs, and wherein each of the gaps is sized to receive the lid sidewall when the lid is fitted over the base.

2. The cell culture device of claim 1, wherein each of the at least two gripping tabs is sized to fit the human finger.

3. The cell culture device of claim 1, wherein the at least two gripping tabs are textured.

4. The cell culture device of claim 1, wherein the base further comprises:
   a bottom panel, wherein the bottom panel is flat; and
   the base sidewall extends upwardly from the bottom panel, wherein the base sidewall is connected to the bottom wall and has a top edge.

5. The cell culture device of claim 1, wherein the base further comprising the base sidewall which has a bottom edge and a top edge, where the top edge is connected to a panel from which one or more wells descend.

6. The cell culture device of claim 1, wherein each of the at least two gripping tabs are semi-oval shaped gripping tabs.

7. A method of using a cell culture device, wherein the cell culture device comprises:
   a base comprising a base sidewall; and
   a lid configured to fit over the base, the lid comprising:
      a top panel; and
      a lid sidewall extending downwardly from the top panel, wherein the lid sidewall is connected to the top panel and has a bottom edge; and
      the base sidewall further has a straight outer wall, wherein the straight outer wall has at least two gripping tabs extending therefrom, wherein each of the at least two gripping tabs have a straight inner side where a gap is present between the straight outer wall of the base sidewall and the straight inner side of each of the at least two gripping tabs, and wherein each of the gaps is sized to receive the lid sidewall when the lid is fitted over the base;
   the method comprises:
      gripping at least two of the gripping tabs when the lid is fitted over the base, and
      moving the gripped base and the fitted lid from a first location to a second location.

8. The method of claim 7, further comprising removing the lid by gripping the lid at a location other than at the at least two gripping tabs.

9. The method of claim 7, wherein the at least two gripping tabs are textured.

10. The method of claim 7, wherein each of the at least two gripping tabs are semi-oval shaped gripping tabs.

* * * * *